(12) United States Patent
Crossland et al.

(10) Patent No.: US 6,362,394 B1
(45) Date of Patent: Mar. 26, 2002

(54) JUVENILE HORMONE OR ONE OF ITS AGONISTS AS A CHEMICAL LIGAND TO CONTROL GENE EXPRESSION IN PLANTS BY RECEPTOR MEDIATED TRANSACTIVATION

(75) Inventors: Lyle Dean Crossland, St. Louis, MO (US); Stephen Arthur Goff, Durham, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/376,107

(22) Filed: Aug. 17, 1999

Related U.S. Application Data

(62) Division of application No. 09/051,103, filed as application No. PCT/EP96/04224 on Sep. 27, 1996, now abandoned.
(60) Provisional application No. 60/006,108, filed on Oct. 10, 1995.

(51) Int. Cl.[7] .......................... C12N 15/82; C12N 15/00
(52) U.S. Cl. ..................... 800/278; 435/375; 435/468
(58) Field of Search .................. 800/278, 288, 800/298, 320.1, 320.3; 435/69.1, 69.7, 468, 320.1, 375; 536/23.1, 24.1

(56) References Cited

U.S. PATENT DOCUMENTS

| 4,981,784 A | 1/1991 | Evans et al. ................ 435/6 |
| 5,071,773 A | 12/1991 | Evans et al. ............ 436/501 |
| 5,171,671 A | 12/1992 | Evans et al. ............ 435/69.1 |

(List continued on next page.)

FOREIGN PATENT DOCUMENTS

| EP | 0 465 024 A | 1/1992 |
| EP | 0 589 841 A | 3/1994 |
| WO | WO 90 08830 A | 8/1990 |
| WO | 90/11273 | 10/1990 |
| WO | 91/12258 | 1/1991 |
| WO | 91/13167 | 2/1991 |
| WO | WO 91 14695 A | 10/1991 |

(List continued on next page.)

OTHER PUBLICATIONS

Harmon et al., Activation of mammalian retinoid X receptors by the insect growth regulator methoprene, Proc. Natl. Acad. Sci. USA, 92: 6157–6160, Jun. 1995.
Loyd et al., Epidermal Cell FateDetermination in Arabidopsis: Patterns Defined by a Steroid–Inducible Regulator, Science, 266:436–439, Oct. 21, 1994.

(List continued on next page.)

*Primary Examiner*—Robert A. Schwartzman
*Assistant Examiner*—Katharine F Davis
(74) *Attorney, Agent, or Firm*—J. Timothy Meigs; Gary M. Pace

(57) ABSTRACT

The present invention is drawn to a method of controlling gene expression in plants. Specifically, the method comprises transforming a plant with a USP receptor expression cassette which encodes a USP receptor and at least one target expression cassette which encodes a target polypeptide. Contacting said transformed plant with juvenile hormone or one of its agonists activates expression of the target polypeptide in the presence of said USP receptor polypeptide. Optionally, additional "secondary" receptor expression cassettes may be used, wherein the secondary receptor expression cassette encodes a receptor polypeptide distinct from USP. The method is useful for controlling various traits of agronomic importance, such as plant fertility. Also disclosed is a method of identifying previously unknown ligands for USP. Substances to be tested are identified by placing them in contact with plant cells transformed with a USP receptor expression cassette and a target expression cassette. The target expression cassette encodes a reporter polypeptide whose expression can be determined quantitatively or qualitatively, whereby the test substance is identified as a ligand for USP.

32 Claims, 3 Drawing Sheets

U.S. PATENT DOCUMENTS

Figure 1:
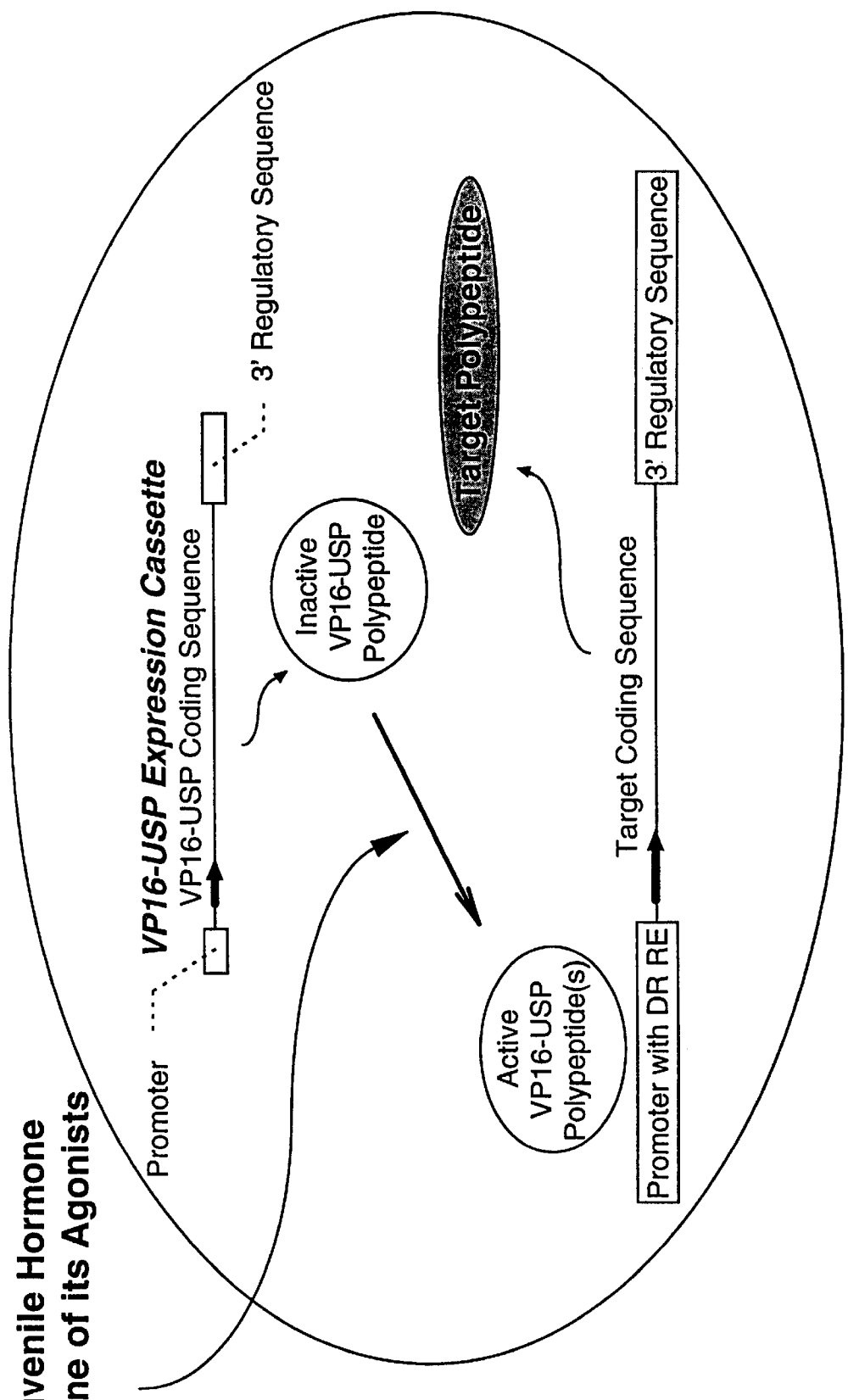

| | | |
|---|---|---|
| 5,534,418 A | 7/1996 | Evans et al. ............... 435/69.1 |
| 5,641,652 A | 6/1997 | Oro et al. .................. 435/69.1 |
| 5,688,691 A | 11/1997 | Oro et al. ................... 435/348 |
| 5,700,650 A | 12/1997 | Mak et al. .................... 435/7.1 |
| 5,700,682 A | 12/1997 | Mak et al. .............. 435/252.3 |
| 5,707,798 A | 1/1998 | Brann et al. .................... 435/6 |
| 5,707,800 A | 1/1998 | Mangelsdorf et al. ......... 435/6 |
| 5,710,004 A | 1/1998 | Evans et al. .................... 435/6 |
| 5,874,534 A | 2/1999 | Vegeto et al. ............... 530/350 |
| 5,880,333 A | 3/1999 | Goff et al. .................. 800/288 |

FOREIGN PATENT DOCUMENTS

| | | |
|---|---|---|
| WO | 93/03162 | 8/1992 |
| WO | 93/06215 | 4/1993 |
| WO | WO 93 09237 A | 5/1993 |
| WO | WO 93 21334 A | 10/1993 |
| WO | WO 93 23431 | 11/1993 |
| WO | WO 94 01558 A | 1/1994 |
| WO | WO 94 21804 A | 9/1994 |
| WO | WO 95 20668 A | 8/1995 |
| WO | 96/37609 | 5/1996 |
| WO | WO 96 27673 A | 9/1996 |
| WO | 97/38117 | 3/1997 |

OTHER PUBLICATIONS

Seagraves, Cell, 67:225–228(1991).
Oro et al., Nature, 374:298–301 (1990).
Thomas et al., Nature, 362:471–475(1993).
Oro et al., Current Opinion in Genetics and Development, 2:269–274(1992).
Henrich et al., Nucleic Acids Research, 18:4143–4148(1990).
Aoyama et al., Plant Journal 11(3): 605–612 1997.
Durand et al., Cell 71:73–85(1992).
Heinrich et al., Insect Biochem Molec. Biol. 25(8):881–897(1995).
Jones et al., PNAS(1997) 94: 13499–13503.
Palli et al., PNAS(1994) 91: 6191–6195.
Prestwich et al., Insect BiochemMol. Biol. 24(8):747–761(1994).
Riddiford, Receptor vol. 3:203–209(1993 Humana Press Inc).
Schena et al., PNAS(1991) 88: 10421–10425.
Sutherland, PNAS(1995).
Sutherland et al. PNAS 92: 7966–7970 1995.
Christianson et al., Biochemical and Biophysical Research Communications, 193(3):1318–1323 (1993).

Juvenile Hormone or one of its Agonists

Juvenile Hormone or one of its Agonists

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 42 base pairs
      (B) TYPE: nucleic acid
      (C) STRANDEDNESS: single

```
            (D) TOPOLOGY: linear (ii) MOLECULE TYPE: other nucleic acid
            (A) DESCRIPTION: /desc = "oligonucleotide SF43"

(iii) HYPOTHETICAL: NO (xi) SEQUENCE DESCRIPTION: SEQ ID NO: 1:

CGCGGATCCT AAACAATGAA GCGGCGCTGG TCGAACAACG GC                    42

(2) INFORMATION FOR SEQ ID NO: 2:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide SF23"

(iii) HYPOTHETICAL: NO (xi) SEQUENCE DESCRIPTION: SEQ ID NO: 2:

CGCGGGATCC ATGCGGCCGG AATGCGTCGT CCCG                             34

(2) INFORMATION FOR SEQ ID NO: 3:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "positive strand (iii) HYPOTHETICAL: NO (xi) SEQUENCE DESCRIPTION: SEQ ID NO: 3:

CGGGGGATCC TAAGTAAGTA AGGTAC                                      26

(2) INFORMATION FOR SEQ ID NO: 4:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "complementary strand (iii) HYPOTHETICAL: NO (xi) SEQUENCE DESCRIPTION: SEQ ID NO: 4:

CTTACTTACT TAGGATCCCC                                             20

(2) INFORMATION FOR SEQ ID NO: 5:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide SF42"

(iii) HYPOTHETICAL: NO
```

(xi) SEQUENCE DESCRIPTION: SEQ ID NO: 5:

CGCGGATCCA TGGACAACTG CGACCAGGAC                                30

(2) INFORMATION FOR SEQ ID NO: 6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide SF37"

(iii) HYPOTHETICAL: NO (xi) SEQUENCE DESCRIPTION: SEQ ID NO: 6:

GCGGGATCCC CCACCGTACT CGTCAATTC                                 29

(2) INFORMATION FOR SEQ ID NO: 7:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide SA115"

(iii) HYPOTHETICAL: NO (xi) SEQUENCE DESCRIPTION: SEQ ID NO: 7:

GTCGAGCTCT CGGATCCTAA AACAATGGCC CCCCCGACCG ATGTC               45

(2) INFORMATION FOR SEQ ID NO: 8:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide SF30"

(iii) HYPOTHETICAL: NO (xi) SEQUENCE DESCRIPTION: SEQ ID NO: 8:

CGCGGATCCA TGGGTCGCGA TGATCTCTCG CCTTC                          35

(2) INFORMATION FOR SEQ ID NO: 9:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 9:

Val Pro Gly Pro Pro Ser Arg Ser Arg Val S er Ile Ser Leu His Ala
1               5                   10                  15

-continued (2) INFORMATION FOR SEQ ID NO: 10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer SF77"

(iii) HYPOTHETICAL: NO (xi) SEQUENCE DESCRIPTION: SEQ ID NO: 10:

GATCCGTAGG GGTCACGAAG TTCACTCGCA          30

(2) INFORMATION FOR SEQ ID NO: 11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer SF78"

(iii) HYPOTHETICAL: NO (xi) SEQUENCE DESCRIPTION: SEQ ID NO: 11:

GATCTGCGAG TGAACTTCGT GACCCCTACG          30

JUVENILE HORMONE OR ONE OF ITS AGONISTS AS A CHEMICAL LIGAND TO CONTROL GENE EXPRESSION IN PLANTS BY RECEPTOR MEDIATED TRANSACTIVATION

This is a division of U.S. application Ser. No. 09/051,103, filed Nov. 12, 1998 now abandoned, which is a §371 of PCT/EP96/04224, filed Sep. 27, 1996 (published Apr. 17,1997, as WO 97/13864), which claims priority to U.S. Provisional Application No. 60/006,108, filed Oct. 10, 1995.

The present invention relates to chemical control of gene expression in plants. In particular, it relates to a method whereby juvenile hormone or one of its agonists is used as a chemical ligand to regulate receptor-mediated expression of a target polypeptide in a plant cell, as well as to transgenic plant cells, plant material or plants and the progeny thereof containing appropriate expression cassettes.

In some cases it is desirable to control the time or extent of expression of a phenotypic trait in plants, plant cells or plant tissue. An ideal situation would be the regulation of expression of such a trait at will, triggered by a chemical that could be easily applied to field crops, ornamental shrubs, etc. One such system of regulating gene expression which could be used to achieve this ideal situation, as yet unknown to be present naturally in plants, is the steroid and thyroid hormone superfamily of nuclear receptors. The steroid and thyroid hormone superfamily of nuclear receptors is found in mammals and insects and is composed of over 100 known proteins. Some of the receptors within this superfamily which are found in mammals are Retinoic Acid Receptor (RAR), Vitamin D Receptor (VDR), Thyroid Hormone Receptor ($T_3R$) and Retinoic X Receptor (RXR). These and other receptors of the superfamily bind to the 5' regulatory region of the target gene and, upon binding of a chemical ligand to the receptor, transactivate target gene expression.

In addition to the receptors found in mammals as described above, receptors of similar structure and activity have been indentified in the insect Drosophila. Koelle et al., *Cell* 67: 59 (1991); Christianson and Kafatos, *Biochem. Biophys. Res. Comm.* 193:1318 (1993); Henrich et al., *Nucleic Acids Res.* 18: 4143 (1990). The Ecdysone Receptor (EcR) binds the insect steroid hormone 20-hydroxyecdysone and, when heterodimerized with the product of the Ultraspiracle gene (USP), transactivates gene expression. Additional chemical ligands besides 20-hydroxyecdysone, such as hormone agonists, will also bind to EcR under similar conditions and cause transactivation of a target gene.

USP has also been shown to be a member of the steroid and thyroid superfamily of nuclear receptors although it is considered an "orphan" receptor since its ligand has not been identified (Seagraves, *Cell* 67:225–228 (1991)). USP is related in sequence to RXRα (Oro et al, *Nature*, 347:298–301 (1990)), and RXR is capable of forming heterodimers with EcR (Thomas et al., *Nature* 362: 471–475 (1993)). Methoprene and its derivative methoprene acid, which are juvenile hormone agonists, has been shown to transcriptionally activate a recombinant reporter gene in both insect and mammalian cells by acting through RXRα (Harmon et al., *Proc. Natl. Acad. Sci.* 92:6157–6160 (1995)). Juvenile hormone, however, does not induce RXRα-mediated transactivation (Harmon et al.) To date, there has been no definitive evidence for a nuclear juvenile hormone receptor (Harmon et al.; Henrich and Brown, *Insect Biochem. Molec. Biol.* 25:881–897 (1995)), although it has been suggested that the orphan receptor USP may be a candidate (Harmon et al.; see also Seagraves; Oro et al., *Current Opinion in Genetics and Development* 2:269–274 (1992)).

Juvenile hormone and its agonists offer previously unrecognized opportunities for chemical control of gene expression in plants since these chemicals are already known for agricultural use. What has been lacking to date is a means by which these chemicals can be used to induce transactivation of a target gene in a transgenic plant. Juvenile hormone and its agonists have herein shown to be ligands for the orphan receptor USP. This discovery permits the implementation of gene control strategies for plants which utilizes a nuclear receptor that does not occur naturally in plants. This means that the only effect of the application of juvenile hormone or one of its agonists will be to induce expression of a genetically engineered target gene. As is demonstrated by the present invention, USP receptor polypeptides, and the plant-expressible genes that encode them, have been developed which function in plant cells to control expression of a target polypeptide wherein the USP receptor polypeptide activates the 5' regulatory region of a target expression cassette in the presence of juvenile hormone or one of its agonists. Such a method of controlling gene expression in plants is useful for controlling various traits of agronomic importance, such as plant fertility.

The present invention is drawn to a method of controlling gene expression in plants. Specifically, the method comprises transforming a plant with a USP receptor expression cassette which encodes a USP receptor polypeptide, with at least one target expression cassette which encodes a target polypeptide, and optionally with a secondary receptor expression cassette encoding a secondary receptor polypeptide distinct from the USP receptor polypeptide. Contacting said transformed plant with juvenile hormone or one of its agonists activates or inhibits expression of the target polypeptide in the presence of said USP receptor polypeptide. Optionally, additional "secondary" receptor expression cassettes may be used, wherein the secondary receptor expression cassette encodes a receptor polypeptide distinct from USP. The method is useful for controlling various traits of agronomic importance, such as plant fertility.

The invention is further drawn to transgenic plants comprising a USP receptor expression cassette and a target expression cassette capable of activation by juvenile hormone or one of its agonists. Also encompassed by the invention is a method of identifying previously unknown ligands for USP which are effective in a plant cell environment. Substances to be tested are identified by placing them in contact with plant cells transformed with a USP receptor expression cassette and a target expression cassette. The target expression cassette encodes a reporter polypeptide whose expression can be determined quantitatively or qualitatively, whereby the test substance is identified as a ligand for USP.

FIG. 1 gives a pictoral representation of a plant cell comprising a VP16-USP receptor expression cassette and a target expression cassette with a direct repeat response element present in the 5' regulatory region. In the presence of juvenile hormone or one of its agonists, the VP16-USP receptor activates expression of the target polypeptide.

Figure 2:
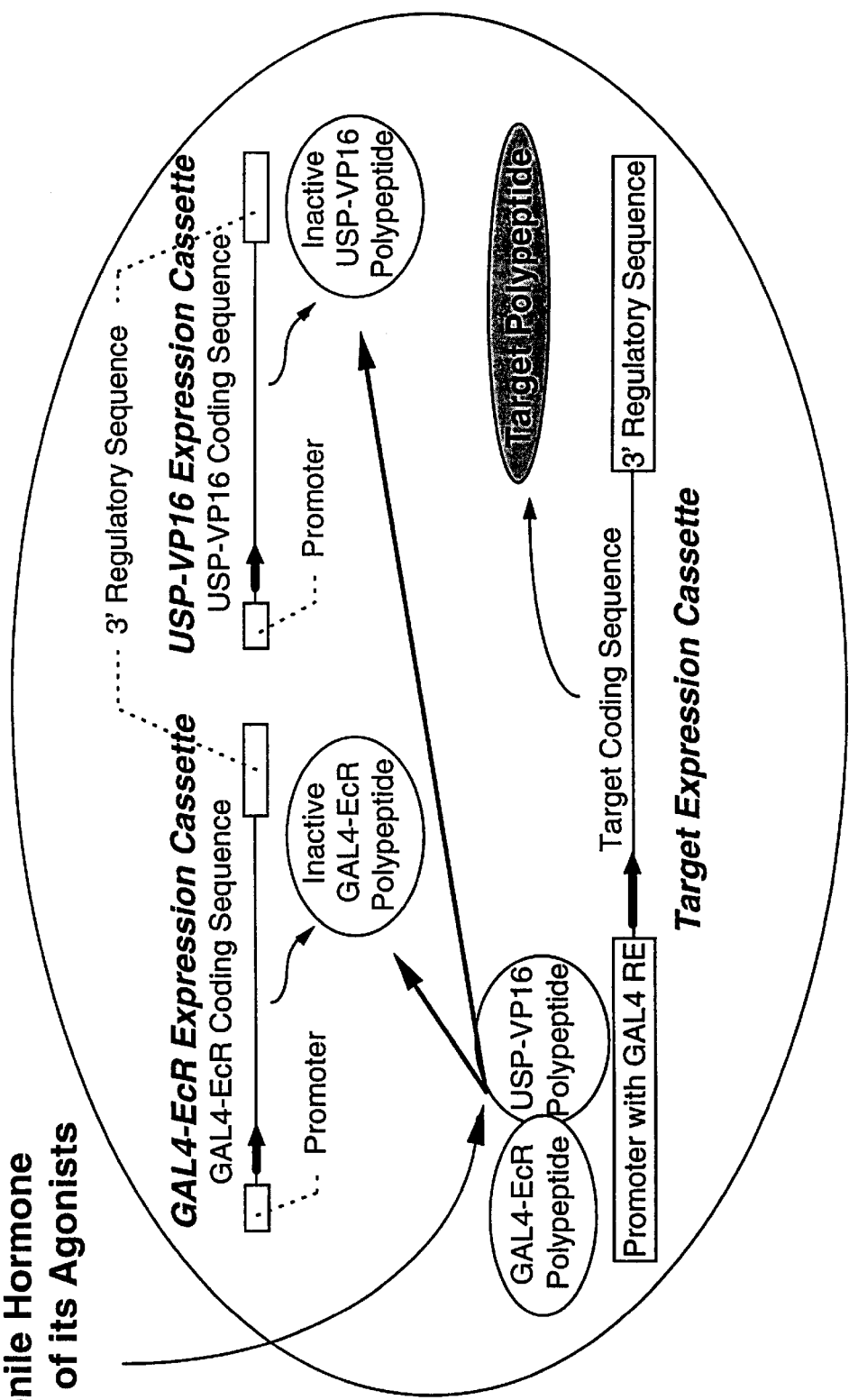

FIG. 2 gives a pictoral representation of a plant cell comprising both a USP-VP16 and a GAL4-EcR receptor expression cassette. Upon exposure to juvenile hormone or one of its agonists, the activation of expression of the target polypeptide caused by the combination of the GAL4-EcR and USP-VP16 receptor polypeptides is reversed.

Figure 3:
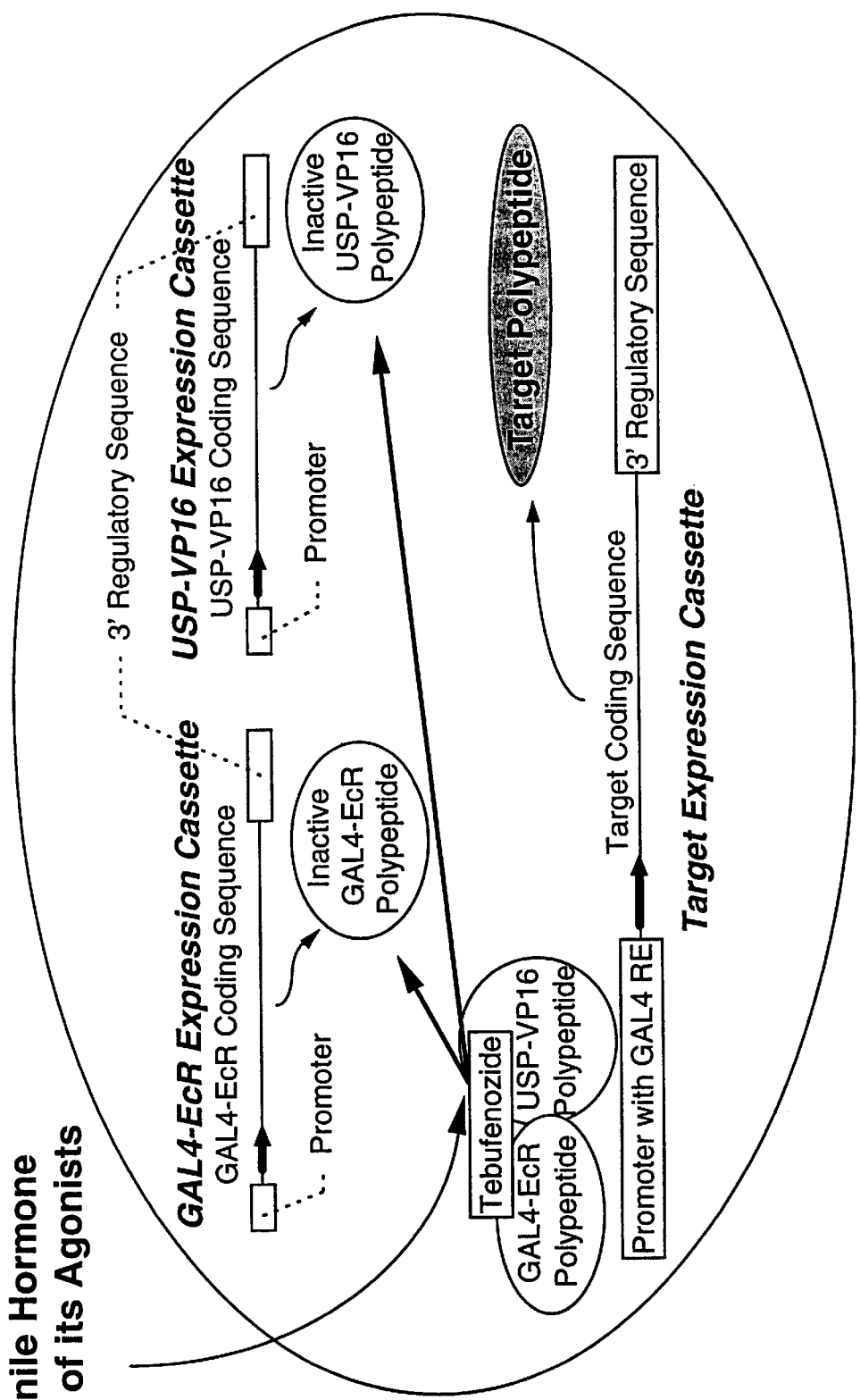

FIG. 3 corresponds to FIG. 2, except that the chemical ligand tebufenozide (also known as RH 5992) is present. In the presence of juvenile hormone or one of its agonists, also activation is reversed under these circumstances.

"Juvenile hormone" refers to a class of chemical compounds which are produced by insects. Juvenile hormone controls larval metamorphosis by causing the retention of the insect's juvenile characteristics and consequent prevention of maturation. The action of juvenile hormone is manifested biologically as behavioral, biochemical or molecular effects. Several naturally occurring juvenile hormones have been isolated and characterized. Agonists of juvenile hormone refers to a class of compounds which exhibit one or more of the biological activities of juvenile hormone. Agonists of juvenile hormone may or may not be structural analogs of juvenile hormone. Also included within this description are those compounds that may be metabolic precursors of the compound which directly produces the abovementioned juvenile hormone-like biological effects. For example, methoprene is a metabolic precursor of methoprene acid, which in turn directly produces the juvenile hormone-like biological effects observed upon application of methoprene.

"Receptor polypeptide" as used herein refers to polypeptides which can either activate or inhibit the expression of a target polypeptide in response to an applied chemical ligand. The receptor polypeptide is comprised of a ligand binding domain, a DNA binding domain and a transactivation domain. The ligand binding domain comprises a sequence of amino acids whose structure binds non-covalently a complementary chemical ligand. Hence, a ligand binding domain and its chemical ligand form a complementary binding pair. The DNA binding domain comprises a sequence of amino acids which binds non-covalently a specific nucleotide sequence known as a response element (RE). One ore more response elements are located in the 5' regulatory region of the target expression cassette. Each RE comprises a pair of half-sites, each half-site having a 5–6 base pair core where a single DNA binding domain recognizes a single half-site. The half-sites may be arranged in relative linear orientation to each other as either direct repeats, palindromic repeats or inverted repeats. The nucleotide sequence, spacing and linear orientation of the half-sites determine which DNA binding domain or domains will form a complementary binding pair with the response element. The transactivation domain comprises one or more sequences of amino acids acting as subdomains which affect the operation of transcription factors during preinitiation and assembly at the TATA box. The effect of the transactivation domain is to allow repeated transcription initiation events, leading to greater levels of gene expression.

A "receptor expression cassette" comprises a nucleotide sequence for a 5' regulatory region operably linked to a nucleotide sequence which encodes a receptor polypeptide and an untranslated 3' termination region (stop codon and polyadenylation sequence). The 5' regulatory region is capable of promoting expression in plants.

"USP" refers to the receptor Ultraspiracle found in Drosophila. It is also known as "XR2C", it has been isolated and cloned, and its ligand binding domain has been identified by sequence homology to known ligand binding domains (Henrich et al., *Nucleic Acids Research* 18: 4143–4148 (1990)), although the chemical ligand or ligands which bind to it have been heretofore unknown. The designation "USP" as used herein refers to native forms of the receptor, as well as mutant or chimeric forms thereof. This includes but is not limited to those mutant or chimeric forms disclosed herein, as well as chimeric forms of USP which comprise at minimum the ligand binding domain of native USP and mutants thereof. More than one form of USP may be used simultaneously in the present invention.

A "secondary receptor expression cassette" comprises a nucleotide sequence for a 5' regulatory region operably linked to a nucleotide sequence which encodes a receptor polypeptide distinct from USP operably linked to a 3' termination region. The secondary receptor expression cassette includes but is not limited to EcR, RXR, and Drosophila Hormone Receptor 38 (DHR38) (Sutherland et al., *Proc. Natl. Acad. Sci.* 92: 7966–7970 (1995)) as well as mutant and chimeric forms thereof.

A "moiety" refers to that portion of a receptor polypeptide that is derived from the indicated source. For example, "USP-moiety" refers to that portion of the receptor polypeptide that was derived from the native Ultraspiracle receptor. Moiety as used here may comprise one or more domains, and at minimum comprises the ligand binding domain of the receptor for which the moiety is named.

The term "chimeric" is used to indicate that the receptor polypeptide is comprised of domains at least one of which has an origin that is heterologous with respect to the other domains present. "Heterologous" means that one or more of the domains present in a receptor polypeptide differ in their natural origin with respect to other domains present. For example, if the transactivation domain from the herpes simplex VP16 protein is operably linked to the USP receptor from Drosophila, then the VP16 transactivation domain is heterologous with respect to the USP-moiety. Furthermore, if a domain from USP is operably linked to a domain from RXR to make a functional receptor, then the chimeric fusion would have domains that are heterologous to each other. These chimeric receptor polypeptides are encoded by nucleotide sequences which have been operably linked resulting in a coding sequence which does not occur naturally. The chimeric receptor polypeptides of the present invention are referenced by a linear nomenclature from the N-terminal to C-terminal portion of the polypeptide. Using this nomenclature, a chimeric receptor polypeptide having the transactivation domain from VP16 added to the N-terminal region of the USP receptor would be designated as VP16-USP. Conversely, if VP16 was added to the C-terminus region of the USP receptor the chimeric receptor polypeptide would be designated USP-VP16.

Gene constructions are denominated in terms of a 5' regulatory region and its operably-linked coding sequence, where the 5' regulatory region is designated before a slash mark (/) and the coding sequence designated after the slash mark. For example, the gene construction 35S/USP-VP16 designates the 35S promoter of Cauliflower Mosaic Virus operably linked to the DNA sequence encoding the chimeric receptor USP-VP16, where the transactivation domain of VP16 has been added to the C-terminal region of USP. When reference is made to the receptor polypeptide, no promoter is designated. For example, the above gene construction encodes the USP-VP16 polypeptide.

A "target expression cassette" comprises a nucleotide sequence for a 5' regulatory region operably linked to a nucleotide sequence which encodes a target polypeptide whose expression is either activated or inhibited by the receptor polypeptides in the presence of a chemical ligand. The 5' regulatory region of the target gene comprises a core promoter sequence, an initiation of transcription sequence and the response element or response elements necessary for complementary binding of the receptor polypeptides. The 5' regulatory region is capable of promoting expression in plants. The target expression cassette also possesses a 3' termination region (stop codon and polyadenylation sequence).

Juvenile hormones I, II, III and O are known, as is a substituted version of I. E.g. *Fundamentals of Insect*

*Physiology*, M. S. Blum, Ed., John Wiley & Sons, New York, 1985. Juvenile hormone I has the formula methyl 10,11-epoxy-7-ethyl-3,11-dimethyl-trans-2,6-tridecadienoate. The structure of juvenile hormone I is shown below.

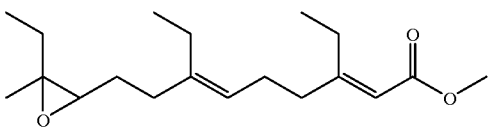

Juvenile hormone agonists are compounds which exhibit one or more of the biological activities of juvenile hormone. Compounds having this property which bear a structural relationship to juvenile hormone include but are not limited to kinoprene, methoprene, hydroprene and methoprene acid. The structure of kinoprene as one example of these juvenile hormone agonists is shown below.

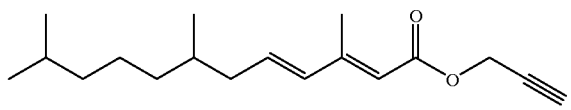

Juvenile hormone agonists which are not structurally related to juvenile hormone are also known. Such compounds include, but are not limited to, the polycyclic, non-isoprenoid compound fenoxycarb, which is a well-known juvenile hormone agonist. The formula for fenoxycarb is ethyl [2-(4-phenoxyphenoxy)ethyl]carbamate. The structure of fenoxycarb is shown below.

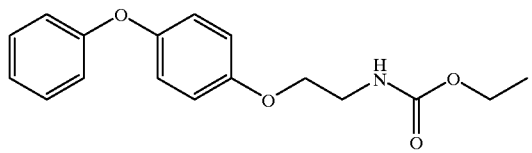

Another juvenile hormone agonist useful in the invention is the compound diofenolan, a diphenyl ether compound. The formula for diofenolan is 4-(2-ethyl-1,3-dioxolan-4-ylmethoxy)phenyl phenyl ether. This compound has known juvenile hormone activity and is expected to function in a manner analogous to that of the compounds fenoxycarb or methoprene.

The use of juvenile hormone agonists in the present invention offer several advantages. First, the compounds are synthetic and readily available. Second, many of these compounds have the benefit of already being examined for agricultural production, making such chemicals "ready-to-use" for field application to crops.

The present invention makes use of the finding that juvenile hormone or one of its agonists act as chemical ligand for the USP receptor. A chemical ligand for USP, previously unknown, has been used in the present invention In conjunction with plant-expressible USP receptor expression cassettes and appropriate target expression cassettes to create a novel method of controlling gene expression in plants.

Many of the insect growth regulators have been found to inhibit molting in insects and are likely to function directly on the receptors involved in Initiating molting. Such insect growth regulators include but are not limited to triflumuron ((1-(2-chlorobenzoyl)-3-(4-trifluoromethoxyphenyl)urea), hexamflumuron (1-[3,5-dichloro-4-(1,1,2,2-tetrafluoroethoxy)phenyl]-3-(2,6-difluorobenzoyl)urea), teflubenzuron (1-(3,5-dichloro-2,4-difluorophenyl)-3-(2,6-difluorobenzoyl)urea), flufenoxuron (1-[4-(2-chloro-α,α,α-trifluro-p-tolyloxy)-2-fluorophenyl]-3-(2,6-difluorobenzoyl)urea), flucycloxuron (1-[α-(4-chloro-α-cyclopropylbenzylideneamino-oxy)-p-tolyl]-3-(2,6-difluorobenzoyl)urea), and lufenuron (1 -[2,5-dichloro-4-(1,1,2,3,3,3-hexafluoropropoxy)phenyl]-3-(2,6-difluorobenzoyl)urea). Additional benzoylphenylurea insecticides, including but not limited to diflubenzuron and chlorfluzuron, may also be used with the present invention.

Retinoic acid or its derivatives may also be a useful ligand to control gene expression in transgenic plants. Retinoic acid has recently been shown to activate a heterologously-expressed USP gene product in cultured mammalian cell lines (Harmon et al.). Insect receptors may therefore be regulated by the application of retinoic acid derivatives to transgenic plants carrying the appropriate combination of receptor(s) and target gene constructs, as discussed below.

Natural sources may also act as ligands for insect receptors expressed in transgenic plants such as transgenic maize or wheat. A number of plants have been found to synthesize compounds which either accelerate or inhibit insect molting. For example, one of the most active ecdysteroids, muristerone, is isolated from plant sources. Many families of plants are known to produce either ecdysteroid or juvenile hormone activities.

Juvenile hormone antagonists may also serve as ligands to regulate gene expression in transgenic plants. Examples of such ligands are ethyl 4-[2-tert-butylcarboxyloxy]benzoate; bisthiocarbamate, 5-methoxy-6-[1-(4-methoxyphenyl)ethyl]-1,3-benzodioxole or ethyl E-3-methyl2-dodecenoate. Such antagonist ligands could serve to activate low basal expression of transgenes or inhibit high basal gene expression in a heterologous plant system expressing modified insect receptor(s).

The method of the present invention comprises transforming a plant cell or plant with a USP receptor expression cassette and a target expression cassette. Expressing, in the presence of juvenile hormone or one of its agonists, USP receptor polypeptide within the obtained plant cells, plants or progeny thereof activates the 5' regulatory region of a target expression cassette within the transgenic cells or plants (FIG. 1). Juvenile hormone or one of its agonists, having been here recognized as binding to the ligand binding domain of USP, are essential to the present invention.

Controlling the expression of a target expression cassette can also be achieved by optionally expressing within a plant an additional secondary receptor polypeptide or polypeptides distinct from USP (FIGS. 2 and 3). Examples of additional secondary receptor polypeptides encompassed by the invention include, but are not limited to, EcR, RXR, DHR38 ([Sutherland et al., *Proc. Natl. Acad. Sci.* 92: 7966–7970 (1995)) as well as mutant or chimeric forms thereof. The use of these receptors for mediating ligand-induced transactivation is described in International Application No. PCT/EP 96/00686, filed Feb. 19, 1996 and herein incorporated by reference.

The ligand binding domain of the USP receptor polypeptide provides the means of chemical control of the activation of the 5' regulatory region of the target expression cassette by juvenile hormone or one of its agonists. USP is similar to the steroid receptor RXRα, which has as a chemical ligand 9-cis-retinoic acid. USP has also been shown to form heterodimers with the EcR receptor polypeptide and regulate the expression of a target polypeptide in transformed mice kidney cells in response to the application of ecdysone, an insect hormone which binds to EcR and is unrelated to juvenile hormone and its agonists. (WO 94/01558). The receptor USP and its ligand binding domain have been found in the present Invention to be particularly useful for controlling target polypeptide expression in plants in response to the application of juvenile hormone or one of its agonists, as described in the examples below.

Chimeric forms of USP receptor polypeptides may also be used in the present invention to activate expression of a target polypeptide in the presence of juvenile hormone or one of its agonists. Either the DNA binding domain or the transactivation domain of a chimeric USP receptor polypeptide may be chosen from a heterologous source based upon their effectiveness for transactivation or DNA binding. Said domains of the chimeric receptor polypeptide may be obtained from any organism, such as plants, insects and mammals which have similar transcriptional regulating functions. In one embodiment of the invention, these domains are selected from other members of the steroid and thyroid hormone superfamily of nuclear receptors. The use of chimeric receptor polypeptides has the benefit of combining domains from different sources. Chimeric USP receptor polypeptides as provided herein offer the advantage of combining optimum transactivating activity or altered RE binding or recognition of a specific response element with juvenile hormone or one of its agonists as ligand. Thus, a chimeric polypeptide may be constructed that is tailored for a specific purpose. These chimeric receptor polypeptides also provide improved functionality in the heterologous environment of a plant cell.

It is also considered a part of the present invention that the transactivation, ligand-binding and DNA-binding domains may be assembled in the chimeric receptor polypeptide in any functional arrangement. For example, where one subdomain of a transactivation domain is found at the N-terminal portion of a naturally-occuring receptor, the chimeric receptor polypeptide of the present invention may include a transactivation subdomain at the C-terminus in place of, or in addition to, a subdomain at the N-terminus. Chimeric receptor polypeptides as disclosed herein may also have multiple domains of the same type, for example, more than one transactivation domain (or two subdomains) per receptor polypeptide.

Thus, one embodiment of the invention provides a USP receptor polypeptide which activates expression of a target polypeptide in the presence of juvenile hormone or one of its agonists and which also possesses superior characteristics for transactivation. Transactivation domains can be defined as amino acid sequences that increase productive transcription initiation by RNA polymerases. (See generallyPtashne, *Nature* 335: 683–689 (1988)). Different transactivation domains are known to have different degrees of effectiveness in their ability to increase transcription initiation. In the present invention it is desirable to use transactivation domains which have superior transactivating effectiveness in plant cells in order to create a high level of target polypeptide expression in response to the presence of a juvenile hormone or one of its agonists. Transactivation domains which have been shown to be particularly effective in the method of the present invention include but are not limited to VP16 (isolated from the herpes simplex virus). In one preferred embodiment of the present invention, the transactivation domain from VP16 is operably linked to a USP-moiety to create a chimeric USP receptor polypeptide for controlling target polypeptide expression in plants. Other transactivation domains will also be effective.

The DNA binding domain is a sequence of amino acids which has certain functional features which are responsible for binding of the USP receptor polypeptide to a specific sequence of nucleotides, called the response element, present in the 5' regulatory region of the target expression cassette. The structure of DNA binding domains for the steroid and thyroid superfamily of nuclear receptors is highly conserved from one species to another, and consequently there is limited variation in the response elements used to form a complementary binding pair. (Evans, *Science* 240: 889–895 (1988)). Nevertheless, considerable flexibility can be introduced into the method of controlling gene expression by using the response elements in other ways. In a preferred embodiment of the invention, multiple copies and preferably between 1 and 11 copies of the appropriate response element are placed in the 5' regulatory region, which allows multiple sites for binding of USP or optional secondary receptor polypeptides resulting in a greater degree of activation.

Further flexibility in the gene control method can be achieved by changing the linear orientation or position of the response elements in the 5' regulatory region. The response elements which are recognized by Class II receptor proteins have a "dyad" symmetry composed of two "half-sites." (Evans, *Science* 240: 889–895 (1988)). Each receptor polypeptide binds to a "half-site." These "half-sites" may be oriented in either a direct repeat, inverted repeat or palindromic fashion. In one embodiment of the present invention, more than one USP receptor polypeptide molecule recognizes a direct repeat (DR) response element, whereby the activation of the target expression cassette is achieved in the presence of a juvenile hormone or one of its agonists.

Additional flexibility in controlling gene expression by the present invention may be obtained by using DNA binding domains and response elements from other transcriptional activators, which include but are not limited to the LexA or GAL4 proteins. The DNA binding domain from the LexA protein encoded by the lexA gene from *E. coli* and its complementary binding site (Brent and Ptashne, *Cell* 43:729–736, (1985), which describes a LexA/GAL4 transcriptional activator) can be utilized. Another useful source is form the GAL4 protein of yeast (Sadowski et al. *Nature* 335: 563–564 (1988), which describes a GAL4-VP16 transcriptional activator). In one preferred embodiment of the invention, a chimeric version of the optional secondary receptor polypeptide is constructed by fusing the GAL4 DNA binding domain to a moiety containing the ligand binding domain from EcR.

The 5' regulatory region of the USP and optional secondary receptor expression cassettes further comprise a promoter which permits expression in plant tissues and cells. Appropriate promoters are chosen for the receptor expression cassettes so that expression of the receptor polypeptides may be constitutive, developmentally regulated, tissue specific, cell specific or cell compartment specific. Promoters may also be chosen so that expression of the receptor polypeptides themselves can be chemically-induced in the plant, thereby increasing the level of promoter induction by ligand. By combining promoter elements which confer specific expression with those conferring chemically-induced expression, the receptor polypeptides may be expressed or activated within specific cells or tissues of the plant in response to chemical application.

The nucleotide sequence which encodes the receptor polypeptide may be modified for improved expression in plants, improved functionality, or both. Such modifications include, but are not limited to, altering codon usage, insertion of introns or creation of mutations. In one embodiment of the invention, expression cassettes comprising an anther-specific or pistil-specific promoter operably linked to a nucleotide sequence which encodes a USP receptor polypeptide are used to activate the expression of a target polypeptide in the presence of juvenile hormone or one of its agonists.

Target polypeptides whose expression is activated by the receptor polypeptides in the presence of a juvenile hormone or one of its agonists are also disclosed. The expression of any coding sequence may be controlled by the present invention, provided that the promoter operably linked to said coding sequence has been engineered to contain the response element or response elements which are complementary to the DNA binding domain of the USP receptor, and, optionally, the response element or response elements needed for the secondary receptor. For example, target polypeptides which are useful for controlling plant fertility, are activated by the USP receptor polypeptide in the presence of a juvenile hormone or one of its agonists.

Mutants of the USP receptor polypeptide are also encompassed by the invention. Mutants can be prepared which have the property of a reduced level of background activation of the target expression cassette so that induction is large relative to the uninduced background expression. Furthermore, mutants can be developed which are altered in their binding to juvenile hormone or one of its agonists. Mutants having altered binding properties will respond to different agonists in ways unique to those agonists. For example, mutant USP receptors can be developed which respond only to the agonist fenoxycarb and not hydroprene, thus distinguishing between the isoprenoid and non-isoprenoid juvenile hormone agonists. Useful methods of mutagenesis such as chemical mutagenesis or site-directed mutagenesis are known in the art.

In another method, mutant receptor polypeptides are prepared by PCR mutagenesis of the nucleotide sequence encoding the ligand binding domain of USP. These mutant receptor polypeptides are expressed in a host organism that lends itself to convenient screening and isolation techniques, such as yeast. Screening for mutant receptor polypeptides that exhibit decreased basal activity and a greater fold induction in such a host organism will, however, only provide candidates for further testing in plant cells, since it is clear from work with the glucocorticoid receptor (GR) that although receptors from the steroid and thyroid hormone superfamily can function in yeast, it is not predictive of functionality in transgenic plants (Lloyd et al., *Science* 226: 436 (1994)). Further limiting the application of results from yeast is the observation that yeast cells which express GR do not respond to the commonly used chemical ligand dexamethasone, while this ligand is functional in other heterologous systems (Schena et al., *Proc. Natl. Acad. Sci. USA* 88: 10421–10425 (1991)).

Further testing in plant cells is accomplished by preparing receptor expression cassettes which encode the mutated receptor polypeptides and transforming them into plant cells in combination with a target expression cassette. The transformed plant cells are tested for activation of the 5'-regulatory region of the target expression cassette by the mutant receptor polypeptides in the presence of juvenile hormone or one of its agonists. Mutant receptor polypeptides which ellicit low basal expression of a target polypeptide in the absence of juvenile hormone or one of its agonists and high expression of target polypeptide in the presence of juvenile hormone or one of its agonists are useful for controlling gene expression in plants.

As described above, the method of the present invention can be used to statistically increase gene expression over a minimal, basal level. However, the present invention can also be used for statistically decreasing or inhibiting the activation of gene expression which has been mediated by a complex formed by receptors such as USP and EcR. The control of gene expression in plants mediated by such receptor complexes is the subject PCT/EP 96/00686, filed Mar. 3, 1995, herein incorporated by reference. Reversal of activation mediated by these receptor complexes is caused by the presence of a juvenile hormone or one of its agonists, which are the chemical ligands for the USP receptor polypeptide (See FIGS. 2 and 3). In the presence of juvenile hormone or one of its agonists, the USP:EcR complex is disrupted, thereby reversing the activation. For example, in a transgenic plant expressing USP and GAL4-EcR-C1 receptor polypeptides and comprising a target expression cassette having a GAL4 binding site element, the activation of gene expression of the target polypeptide caused by the complex will be reversed. This reversal would occur either in the presence of tebufenozide (also known as RH 5992), or other chemical ligand which binds to the ligand binding domain of EcR, or in the absence of such a chemical ligand.

For expression in plants, suitable promoters must be chosen for both the receptor expression cassettes and the target expression cassette. Unless specifically noted, the promoters discussed below may be used to direct expression in plants of either the receptor polypeptides or the target polypeptide. These promoters include, but are not limited to, constitutive, inducible, temporally regulated, developmentally regulated, chemically regulated, tissue-preferred and tissue-specific promoters. Preferred constitutive promoters include but are not limited to the CaMV 35S and 19S promoters (U.S. Pat. No. 5,352,605). Additionally preferred promoters include but are not limited to one of several of the actin genes, which are known to be expressed in most cell types. The promoter described by McElroy et al., *Mol. Gen. Genet.* 231: 150–160 (1991), can be easily incorporated into the receptor expression cassettes of the present invention and are particularly suitable for use in monocotyledonous hosts. Yet another preferred constitutive promoter is derived from ubiquitin, which is another gene product known to accumulate in many cell types. The ubiquitin promoter has been cloned from several species for use in transgenic plants (e.g. sunflower—Binet et al., *Plant Science* 79: 87–94 (1991); maize—Christensen et al., *Plant Molec. Biol.* 12: 619–632 (1989)). The maize ubiquitin promoter has been developed in transgenic monocot systems and its sequence and vectors constructed for transformation of monocotyledonous plants are disclosed in EP-A-342 926. The ubiquitin promoter is suitable for use in the present invention in transgenic plants, especially monocotyledons. Further useful promoters are the U2 and U5 snRNA promoters from maize (Brown et al., *Nucleic Acids Res.* 17: 8991 (1989)) and the promoter from alcohol dehydrogenase (Dennis et al., *Nucleic Acids Res.* 12: 3983 (1984))

Tissue-specific or tissue-preferential promoters useful in the present invention in plants, particularly maize, are those which direct expression in root, pith, leaf or pollen. Such promoters are disclosed in WO 93/07278, herein incorporated by reference in its entirety. Also useful are promoters which confer seed-specific expression, such as those disclosed by Schernthaner et al., *EMBO J.* 7: 1249 (1988); anther-specific promoters ant32 and ant43D disclosed in EP-A-578 611, herein incorporated by reference in its entirety; anther (tapetal) specific promoter B6 (Huffman et al., *J. Cell. Biochem.* 17B: Abstract #D209 (1993)); pistil-specific promoters such as a modified S13 promoter (Dzelkalns et al., *Plant Cell* 5:855 (1993)).

Also useful in the present invention are chemically-induced promoters. Particular promoters in this category useful for directing the expression of the receptor polypeptides or target polypeptide in plants are disclosed, for example, in EP-A-332 104, herein incorporated by reference in its entirety.

The 5' regulatory region of either the receptor expression cassette or the target expression cassette may also include other enhancing sequences. Numerous sequences have been found to enhance gene expression in transgenic plants. For example, a number of non-translated leader sequences derived from viruses are known to enhance expression. Specifically, leader sequences from Tobacco Mosaic Virus (TMV, the "ω-sequence"), Maize Chlorotic Mottle Virus (MCMV), and Alfalfa Mosaic Virus (AMV) have been shown to be effective in enhancing expression (e.g. Gallie et al. *Nucl. Acids Res.* 15: 8693–8711 (1987); Skuzeski et al *Plant Molec. Biol.* 15: 65–79 (1990)). Other leaders known in the art Include but are not limited to:

Picornavirus leaders, for example, EMCV leader (Encephalomyocarditis 5' noncoding region) (Elroy-Stein, O., Fuerst, T. R., and Moss, B. *PNAS USA* 86:6126–6130 (1989));

Potyvirus leaders, for example, TEV leader (Tobacco Etch Virus) (Allison et al., (1986); MDMV leader (Maize Dwarf Mosaic Virus); *Virology*, 154:9–20);

Human immunoglobulin heavy-chain binding protein (BiP) leader, (Macejak, D. G., and Sarnow, P., *Nature*, 353: 90–94 (1991);

Untranslated leader from the coat protein mRNA of alfalfa mosaic virus (AMV RNA 4), (Jobling, S. A., and Gehrke, L., *Nature*, 325:622–625 (1987);

Tobacco mosaic virus leader (TMV), (Gallie, D. R. et al., *Molecular Biology of RNA*, pages 237–256 (1989); and Maize Chlorotic Mottle Virus leader (MCMV) (Lommel, S. A. et al., *Virology*, 81:382–385 (1991). See also, Della-Cioppa et al., *Plant Physiology*, 84:965–568 (1987).

Various intron sequences have been shown to enhance expression when added to the 5' regulatory region, particularly in monocotyledonous cells. For example, the introns of the maize Adh1 gene have been found to significantly enhance the expression of the wild-type gene under its cognate promoter when introduced into maize cells (Callis et al., *Genes Develep* 1: 1183–1200 (1987)).

In addition to incorporating one or more of the aforementioned elements into the 5' regulatory region of a target expression cassette, other elements peculiar to the target expression cassette may also be incorporated. Such elements include but are not limited to a minimal promoter. By minimal promoter it is intended that the basal promoter elements are inactive or nearly so without binding sites for upstream activators. Such a promoter has low background activity in plants when there is no transactivator present or when enhancer or response element binding sites are absent. One minimal promoter that is particularly useful for target genes in plants is the Bz1 minimal promoter which is obtained from the bronze1 gene of maize. The Bz1core promoter was obtained from the "myc" mutant Bz1-luciferase construct pBz1LucR98 via cleavage at the NheI site located at −53 to −58 (Roth et al., *Plant Cell* 3: 317 (1991)). The derived Bz1core promoter fragment thus extends from −53 to +227 and includes, when used for transgenic maize, the Bz1 intron-1 in the 5' untranslated region.

In addition to promoters, a variety of 3' transcriptional terminators are also available for use in the present invention. Transcriptional terminators are responsible for the termination of transcription and correct mRNA polyadenylation. Appropriate transcriptional terminators and those which are known to function in plants include the CaMV 35S terminator, the tml terminator, the nopaline synthase terminator, the pea rbcS E9 terminator and others known in the art. These can be used in both monocotyledons and dicotyledons.

The expression cassettes of the present invention can be Introduced into the plant cell in a number of art-recognized ways. Those skilled in the art will appreciate that the choice of method might depend on the type of plant, i.e. monocotyledonous or dicotyledonous, targeted for transformation. Suitable methods of transforming plant cells include, but are not limited to, microinjection (Crossway et at, *BioTechniques* 4:320–334 (1986)), eledtroporation (Riggs et al., *Proc. Natl. Acad. Sci. USA* 83:5602–5606 (1986), Agrobacterium-mediated transformation (Hinchee et al., *Biotechnology* 6:915–921 (1988)), direct gene transfer (Paszkowski et al., *EMBO J.* 3:2717–2722 (1984)), and ballistic particle acceleration using devices available from Agracetus, Inc., Madison, Wis. and BioRad, Hercules, Calif. (see, for example, Sanford et al., U.S. Pat. No. 4,945,050; and McCabe et al., *Biotechnology* 6:923–926 (1988)). Also see, Weissinger et al., *Annual Rev. Genet.* 22:421–477 (1988); Sanford et al., *Particulate Science and Technology* 5:27–37 (1987)(onion); Christou et a., *Plant Physiol.* 87:671–674 (1988)(soybean); McCabe et al., *Bio/Technology* 6:923–926 (1988)(soybean); Datta et al., *Bio/Technology* 8:736–740 (1990)(rice); Klein et al., *Proc. Natl. Acad. Sci. USA*, 85:4305–4309 (1988)(maize); Klein et al., *Bio/Technology* 6:559–563 (1988)(maize); Klein et al., *Plant Physiol.* 91:440–444 (1988)(maize); Fromm et al., *Bio/Technology* 8:833–839 (1990)(maize); and Gordon-Kamm et al., *Plant Cell* 2:603–618 (1990)(maize); Svab et al., *Proc. Natl. Acad. Sci. USA* 87: 8526–8530 (1990) (tobacco chloroplast); Koziel et a., *Biotechnology* 11: 194–200 (1993)(maize); Shimamoto et al., *Nature* 338: 274–277 (1989)(rice); Christou et al., *Biotechnology* 9: 957–962 (1991)(rice); EP-A-332 581 (orchardgrass and other Pooideae); Vasil et al., *Biotechnology* 11: 1553–1558 (1993)(wheat); Weeks et a., *Plant Physiol.* 102: 1077–1084 (1993)(wheat).

One particularly preferred set of embodiments for the introduction of the expression cassettes of the present invention into maize by microprojectile bombardment is described in Koziel et al., *Bio/Technology* 11: 194–200, 1993, herein incorporated by reference in its entirety. An additional preferred embodiment is the protoplast transformation method for maize as disclosed in EP-A-292 435, hereby incorporated by reference in its entirety. One particularly preferred set of embodiments for the introduction of the expression cassettes of the present invention into wheat by microprojectile bombardment can be found in WO 94/13822, herein incorporated by reference in its entirety.

Transformation of plants can be undertaken with a single DNA molecule or multiple DNA molecules (i.e. co-transformation), and both these techniques are suitable for use with the expression cassettes of the present invention. Numerous transformation vectors are available for plant transformation, and the expression cassettes of this invention can be used in conjunction with any such vectors. The selection of vector will depend upon the preferred transformation technique and the target species for transformation.

Many vectors are available for transformation using *Agrobacterium tumefaciens*. These typically carry at least one T-DNA border sequence and include vectors such as pBIN19 (Bevan, *Nucl. Acids Res.* (1984)). In one preferred embodiment, the expression cassettes of the present invention may be inserted into either of the binary vectors pCIB200 and pCIB2001 for use with Agrobacterium. These vector cassettes for Agrobacterium-mediated transformation were constructed in the following manner. pTJS75kan was created by NarI digestion of pTJS75 (Schmidhauser & Helinski, *J Bacteriol.* 164: 446–455 (1985)) allowing excision of the tetracycline-resistance gene, followed by insertion of an AccI fragment from pUC4K carrying an NPTII (Messing & Vierra, *Gene* 19: 259–268 (1982); Bevan et al., *Nature* 304:184–187 (1983); McBride et al., *Plant Molecular Biology* 14: 266–276 (1990)). XhoI linkers were ligated to the EcoRV fragment of pCIB7 which contains the left and right T-DNA borders, a plant selectable nos/nptII chimeric gene and the pUC polylinker (Rothstein et al., *Gene* 53: 153–161 (1987)), and the XhoI-digested fragment was cloned into SalI-digested pTJS75kan to create pCIB200 (see also EP-A-332 104, example 19). pCIB200 contains the following unique polylinker restriction sites: EcoRI, SstI, KpnI, BglII, XbaI, and SalI. The plasmid pCIB2001 is a derivative of pCIB200 which was created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for Agrobacterium-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

An additional vector useful for Agrobacterium-mediated transformation is the binary vector pCIB10, which contains a gene encoding kanamycin resistance for selection in plants, T-DNA right and left border sequences and incorporates sequences from the wide host-range plasmid pRK252 allowing it to replicate in both *E. coli* and Agrobacterium. Its construction is described by Rothstein et al., *Gene* 53: 153–161 (1987). Various derivatives of pCIB10 have been constructed which incorporate the gene for hygromycin B phosphotransferase described by Gritz et al., *Gene* 25: 179–188 (1983). These derivatives enable selection of transgenic plant cells on hygromycin only (pCIB743), or hygromycin and kanamycin (pCIB715, pCIB717).

Methods using either a form of direct gene transfer or Agrobacterium-mediated transfer usually, but not necessarily, are undertaken with a selectable marker which may provide resistance to an antibiotic (e.g., kanamycin, hygromycin or methotrexate) or a herbicide (e.g., phosphinothricin). The choice of selectable marker for plant transformation is not, however, critical to the invention.

For certain plant species, different antibiotic or herbicide selection markers may be preferred. Selection markers used routinely in transformation include the nptII gene which confers resistance to kanamycin and related antibiotics (Messing & Vierra, *Gene* 19: 259–268 (1982); Bevan et al., *Nature* 304:184–187 (1983)), the bar gene which confers resistance to the herbicide phosphinothricin (White et al., *Nucl Acids Res* 18: 1062 (1990), Spencer et al., *Theor Appl Genet* 79: 625–631(1990)), the hph gene which confers resistance to the antibiotic hygromycin (Blochinger & Diggelmann, *Mol Cell Biol* 4: 2929–2931), and the dhfrgene, which confers resistance to methotrexate (Bourouis et al, *EMBO J.* 2:1099–1104 (1983)).

One such vector useful for direct gene transfer techniques in combination with selection by the herbicide Basta (or phosphinothricin) is pCIB3064. This vector is based on the plasmid pCIB246, which comprises the CaMV 35S promoter in operational fusion to the *E. coli* GUS gene and the CaMV 35S transcriptional terminator and is described in WO 93/07278, herein incorporated by reference. One gene useful for conferring resistance to phosphinothricin is the bar gene from *Streptomyces viridochromogenes* (Thompson et al., *EMBO J* 6: 2519–2523 (1987)). This vector is suitable for the cloning of plant expression cassettes containing their own regulatory signals.

An additional transformation vector is pSOG35 which utilizes the *E. coli* gene dihydrofolate reductase (DHFR) as a selectable marker conferring resistance to methotrexate. PCR was used to amplify the 35S promoter (~800 bp), intron 6 from the maize Adh1 gene (~550 bp) and 18 bp of the GUS untranslated leader sequence from pSOG10. A 250 bp fragment encoding the *E. coli* dihydrofolate reductase type II gene was also amplified by PCR and these two PCR fragments were assembled with a SacI-PstI fragment from pBI221 (Clontech) which comprised the pUC19 vector backbone and the nopaline synthase terminator. Assembly of these fragments generated pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus check (MCMV) generated the vector pSOG35. pSOG19 and pSOG35 carry the pUC-derived gene for ampicillin resistance and have HindIII, SphI, PstI and EcoRI sites available for the cloning of foreign sequences.

One of the advantageous aspects of the present invention is Its use in the control of plant fertility under field conditions. Effective fertilization results from the formation of viable zygotes and can be measured as the percentage of seeds forming viable zygotes. According to the present invention fertility can be controlled by incorporating a nucleotide sequence encoding an appropriate target into the target expression cassette, wherein the expression of said target polypeptide interferes with plant fertility, meaning that it statistically reduces or increases plant fertility. In a preferred embodiment of the invention said target polypeptide renders the fertilization process ineffective, meaning that the formation of viable zygotes will be impeded or prevented. Such ineffective fertilization can be measured as the percentage of seeds not forming viable zygotes and may be caused by a variety of means. These include but are not limited to, 1) disruption or alteration of those processes which are critical to formation of viable gametes, 2) pollen or ovules that, if formed, are not functional, or 3) failure of the embryo sac, pistil, stigma or transmitting tract to develop properly. In the present invention, juvenile hormone or one of its agonists are applied to, or brought into contact with, transgenic plants under field conditions, wherein the expression of a target polypeptide is activated, whereby fertilization is rendered ineffective. In another embodiment of the present invention expression of said target polypeptide increases or restores the fertility of a plant.

It is recognized that differing degrees of effective or ineffective fertilization can be achieved with the present invention. In a preferred embodiment more than 80% and more preferably more than 95% of ineffective fertilization can be achieved. The ability to provide variability in the level of fertility allows the invention to be tailored for a variety of agricultural purposes.

Useful coding sequences for the target polypeptide include but are not limited to any sequence which encodes a product capable of rendering fertilization ineffective. These coding sequences can be of either a homologous or heterologous origin. The gene products of those coding sequences include, but are not limited to:

Diphtheria Toxin A-chain (DTA), which inhibits protein synthesis, Greenfield et al., *Proc. Natl. Acad. Sci.:USA*, 80:6853 (1983); Palmiter et al., *Cell*, 50:435 (1987);

Pectate lyase pelE from Erwinia chrysanthemi EC16, which degrades pectin, causing cell lysis. Keen et al., *J. Bacteriology*, 168:595 (1986);

T-urf13 (TURF-13) from cms-T maize mitochondrial genomes; this gene encodes a polypeptide designated URF13 which disrupts mitochondrial or plasma membranes. Braun et al., *Plant Cell*, 2:153 (1990); Dewey et al., *Proc. Natl. Acad. Sci.:USA*, 84:5374 (1987); Dewey et al., *Cell*, 44:439 (1986);

Beta-1,3 glucanase, which causes premature dissolution of the microspore callose wall. Worral et al., *Plant Cell* 4: 759–771 (1992);

Gin recombinase from phage Mu a gene, which encodes a site-specific DNA recombinase which will cause genome rearrangements and loss of cell viability when expressed in cells of plants. Maeser et al., *Mol. Gen. Genet.*, 230:170–176 (1991);

Indole acetic acid-lysine synthetase (iaaL) from *Pseudomonas syringae*, which encodes an enzyme that conjugates lysine to indoleacetic acid (IAA). When expressed in the cells of plants, it causes altered developments due to the removal of IAA from the cell via conjugation. Romano et al., *Genes and Development* 5:438–446 (1991); Spena et al., *Mol. Gen. Genet.*, 227:205–212 (1991); Roberto et al., *Proc. Natl. Acad. Sci.:USA*, 87:5795-5801;

Ribonuclease from *Bacillus amyloliquefaciens*, also known as barnase, digests mRNA in those cells in which it is expressed, leading to cell death. Mariani et al., *Nature* 347: 737–741 (1990); Mariani et al., *Nature* 357: 384–387 (1992); and, CytA toxin gene from *Bacillus thuringiensis israeliensis* which encodes a protein that is mosquitocidal and hemolytic. When expressed in plant cells, it causes death of the cell due to disruption of the cell membrane. McLean et al., *J. Bacteriology*, 169:1017–1023 (1987); Ellar et al., U.S. Pat. No. 4,918,006 (1990).

Such polypeptides also Include Adenine Phosphoribosyltransferase (APRT) Moffatt and Somerville, *Plant Physiol.*, 86:1150–1154 (1988); DNAse, RNAse; protease; salicylate hydroxylase; etc.

It is further recognized that the target expression cassette may comprise a 5' regulatory region operably linked to a nucleotide sequence which, when transcribed, produces an antisense version of a coding sequence critical to the formation of viable gametes, such as APRT. Alternately, ribozymes can be utilized which target mRNA from a gene which is critical to gamete formation or function. Such ribozymes will comprise a hybridizing region of about nine nucleotides which is complementary in nucleotide sequence to at least part of the target RNA and a catalytic region which is adapted to cleave the target RNA. Ribozymes are described in EP-A-321 201 and WO 88/04300 herein incorporated by reference. See, also Haseloff and Gerlach, *Nature*, 334:585–591 (1988); Fedor and Uhlenbeck, *Proc. Natl. Acad. Sci.: USA*, 87:1668–1672 (1990); Cech and Bass, *Ann. Rev. Biochem.*, 55:599–629 (1986); Cech, T. R., 236:1532–1539 (1987); Cech, T. R. *Gene*, 73:259–271 (1988); and, Zang and Cech, *Science*, 231:470–4475 (1986).

It is recognized that the above nucleotide sequences encoding a target polypeptide can also be operably linked to a 5' regulatory sequence which directs its expression in a tissue or cell-specific manner. The means to provide such tissue- or cell-specific expression has been described above. This specificity in expression ensures that the effect of the target polypeptide will be exerted only on those tissues or cells which are necessary for the formation of viable zygotes and will not be deleterious to the plant beyond its effect on fertility.

It is recognized as within the scope of the invention that either male fertility of the transgenic plants, female fertility of the transgenic plants, or both, may be controlled. Male sterility is the failure or inability to produce functional or viable pollen. Male sterility may result from defects leading to the non-formation of pollen or to the lack of functional ability in the pollen when it is formed. Therefore, either pollen is not formed or, if formed, it is either non-viable or otherwise incapable of effective fertilization under normal conditions.

Female sterility is the failure or inability to produce functional or viable megaspores or embryo sacs, or other tissues required for pollen germination, growth or fertilization. Female sterility may result from defects leading to the non-formation of the megaspores or embryo sac, or failure of the ovary, ovule, pistil, stigma, or transmitting tract to develop properly. Therefore, either a viable embryo sac falls to develop, or If formed, it is incapable of effective fertilization under normal conditions.

For example, a transgenic plant can be obtained which expresses USP receptor polypeptide or polypeptides in anthers using an anther-specific promoter operably linked to the appropriate nucleotide sequences. In addition, the transgenic plant will further comprise a target expression cassette having a 5' regulatory sequence comprising the appropriate response element sequence with the core promoter elements from Bz1, operably linked to the coding sequence for the ribonuclease barnase. Upon application of juvenile hormone or one of its agonists to the transgenic plant expressing USP receptor polypeptides activation of the 5' regulatory sequence of the target expression cassette occurs with subsequent production of the target polypeptide barnase. The resulting expression of barnase specifically in the anthers causes cell death and consequent male sterility. A similar combination of receptor polypeptides and target expression cassette, using a pistil-specific promoter operably linked to the nucleotide sequences encoding the receptor polypeptides, can produce female sterility.

Alternatively, a plant can be engineered wherein expression of the target polypeptide restores fertility to a male-sterile or female-sterile plant. For example, a plant can be obtained that expresses the barnase gene under control of the Ant43D, Ant32 or B6 promoter, or as described in Mariani et al., *Nature* 347: 737–741 (1990) and Mariani et al., *Nature* 357: 384–387 (1992), under control of the TA29 promoter. These plants additionally comprise the receptor expression cassettes for USP receptor polypeptide and any optional secondary receptor polypeptide from either the same anther-specific promoter or from a constitutive promoter such as maize ubiquitin, 35S or rice actin promoter. These plants further comprise a target expression cassette having a 5' regulatory sequence comprising the appropriate response element sequence with the core promoter elements from Bz1, operably linked to the coding sequence for the barnase inhibitor barstar. The plants are male-sterile, but upon application of juvenile hormone or one of its agonists activation of the 5' regulatory sequence of the target expression cassette occurs with subsequent production of the target polypeptide barstar. Barstar inhibits the ribonuclease activity of the barnase polypeptide, and anther and pollen development proceeds normally. Fertility is thereby restored.

A similar approach can be used to control female sterility. By utilizing promoters specific for expression in the female reproductive tissues instead of the anther-specific promoters to drive barnase expression, female-sterile plants can be obtained. Induction of the target expression cassette comprising the barstar coding sequence by juvenile hormone or one of its agonists results in restoration of female fertility.

The above approaches can utilize any female- or male-sterility gene for which a restorer gene can be devised. Potential restorer genes other than barstar are described in EP-A-412 911.

The genetic properties engineered into the transgenic plants described above and the seeds thereof are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied. As the growing crop is vulnerable to attack and damages caused by insects or infections as well as to competition by weed plants, measures are undertaken to control weeds, plant diseases, insects, nematodes, and other adverse conditions to improve yield. These include mechanical measures such a tillage of the soil or removal of weeds and infected plants, as well as the application of agrochemicals such as herbicides, fungicides, gametocides, nematicides, growth regulants, ripening agents and insecticides.

Use of the advantageous genetic properties of the transgenic plants and seeds according to the invention can further be made in plant breeding which aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties different breeding measures are taken. The relevant techniques are well known in the art and include but are not limited to hybridization, inbreeding, backcross breeding, multiline breeding, variety blend, interspecific hybridization, aneuploid techniques, etc. Thus, the transgenic plants according to the invention and the seeds thereof can be used for the breeding of improved plant lines which for example increase the effectiveness of conventional methods such as herbicide or pestidice treatment or allow to dispense with said methods due to their modified genetic properties. Alternatively new crops with improved stress tolerance can be obtained which, due to their optimized genetic "equipment", yield harvested product of better quality than products which were not able to tolerate comparable adverse developmental conditions.

In seeds production germination quality and uniformity of seeds are essential product characteristics, whereas germination quality and uniformity of seeds harvested and sold by the farmer is not important. As it is difficult to keep a crop free from other crop and weed seeds, to control seedborne diseases, and to produce seed with good germination, fairly extensive and well-defined seed production practices have been developed by seed producers, who are experienced in the art of growing, conditioning and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides or mixtures thereof. Customarily used protectant coatings comprise compounds such as captan, carboxin, thiram (TMTD®), methalaxyl (Apron®), and pirimiphos-methyl (Actellic®). If desired these compounds are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation. Other methods of application are also possible such as treatment directed at the buds or the fruit.

It is a further aspect of the present invention to provide new agricultural methods such as the methods exemplified above which are characterized by the use of transgenic plants, transgenic plant material, or transgenic seed according to the present invention.

The present invention can be used in any plant which can be transformed and regenerated to a transgenic plant. Male sterility, female sterility, or both, can be controlled by the application of the appropriate chemical ligand. The control of plant fertility is particularly useful for the production of hybrid seed. In order to produce hybrid seed uncontaminated with selfed seed, pollination control methods must be implemented to ensure cross-pollination and not self-pollination. This is usually accomplished by mechanical, genetic or chemical hybridizing agents (CHAs). For example, in maize the current practice is mechanical detasseling of the female (or seed) parent, which is a time consuming and labor intensive process. In wheat, controlling fertility by mechanical means is impractical on a seed production scale, and genetic sources of fertility control are not established. The use of the present invention in the production of hybrid seed offers the advantages of reliability, ease of use and control of either male or female fertility.

The transgenic plants containing the appropriate receptor expression cassettes and target expression cassette can be made homozygous and maintained indefinitely. To obtain hybrid seed, homozygous lines of Parent 1 and Parent 2 are crossed. In one example of using the present invention to produce hybrid seed, Parent 1 is engineered to be male sterile in the presence of juvenile hormone or one of its agonists whereas Parent 2 is engineered to be female sterile in the presence of juvenile hormone or one of its agonists. Contacting both Parent 1 and Parent 2 with juvenile hormone or one of its agonists, the only successful seed production will be a result of Parent 2 pollen fertilizing Parent 1 ovules. In a second example of using the present invention, Parent 1 is engineered to be male-sterile in the absence of juvenile hormone or one of its agonists and Parent 2 is engineered to be female sterile in the absence of juvenile hormone or one of its agonists. Contacting Parent 1 and Parent 2 with juvenile hormone or one of its agonists allows maintenance of each line through self-fertilization. To produce hybrid seed, the two parent lines are interplanted, and only hybrid seed is obtained. Fertility is restored to the progeny hybrid plants by an introduced restorer gene. By these means any desired hybrid seed may be produced.

Chemical-control of plant transgene expression can be useful to regulate either gross developmental changes in the target crop, to change the crop plant to be more compatible with a hostile environment, to alter the flux of specific metabolic pathways, or to simply induce the high-level expression of a single desired protein product. Chemical control of developmental programs in plants may allow the farmer to dictate when specific events such as flower development, leaf or fruit abscission, or other important developmental stages begin. Such chemical control over specific developmental events would allow the farmer greater flexibility in time of planting and harvesting as well as allow him to respond to specific environmental conditions, like the forecast of an early winter or wet spring. Such changes could be made by the control of genes critical to the developmental or conditional response pathway, in analogy to the homeotic genes of Drosophila.

It may also be useful to control gene expression of metabolic pathways. It is believed that only a fixed amount of energy can be expended by the plant and that any enhancement of a specific pathway, such as the biosynthesis of storage proteins, will result in the simultaneous loss of biosynthetic flux through energy-competing pathways, such as synthesis of starch or lipids. In a situation where such changes in biosynthetic pathways were only acceptable after the plant had achieved a certain developmental stage (i.e. mature versus growing), chemical regulation of gene expression could be useful or perhaps even required for specific biosynthetic changes to be achieved.

Chemical regulation of gene expression may be useful to overexpress a specific protein at high levels. Certain proteins are known to be toxic to the cell when expressed in a heterologous host, a foreign subcellular compartment, or even when expressed at an inordinately high level. Chemically-controlling the expression of such proteins may be either advantageous to normal plant growth or even required to obtain sufficient plant mass to justify use of the plant for a biosynthetic protein factory. Proteins that may be useful for large-scale biosynthesis in plants include industrial enzymes, pharmaceutical proteins, antigens, as well as other proteins.

Bioassays for identifying ligands for steroid hormone receptors are known (Evans et al., U.S. Pat. No. 5,298,429). Receptors disclosed are limited to the glucocorticoid, mineralcorticoid, estrogen-related and thyroid hormone receptors. These receptors were transformed into mouse kidney cell cultures (CV-1 or COS cell lines) and tested for their ability to transactivate expression of a chimeric CAT gene in the presence of an appropriate mammalian hormone. Neither transformation of plant cells with these receptors, nor construction of plant-expressible genes, nor receptors other than those which have a mammalian hormone as ligand are disclosed.

USP was suggested to be an "insect retinoid receptor" in Oro and Evans, WO 91/14695. In a prophetic example, XR2C encoding USP is transformed into insect cell cultures (S2 cell line) to transactivate a chimeric CAT gene in response to addition of retinoic acid. The disclosure suggests that insect or animal cells transformed with such "insect retinoid receptors" can be used to screen for compounds which are capable of leading to activation of the receptors. However, Oro et al. later reported that USP is not activated by retinoic acid in Drosophila cell-culture assays, and under conditions in which RXR is responsive, USP does not respond to any of the retinoids or juvenoids tested, including methoprene acid (Harmon et al. and references therein).

With the discovery herein that juvenile hormone and its agonists are the ligand for USP, and that USP can be used to activate target gene expression in the presence of juvenile hormone or one of its agonists in plant cells, it is now possible to discover new ligands for the USP receptor which are effective in a plant cell environment. Screening is based on the expression of a target expression cassette encoding a receptor-regulated reporter gene in transgenic plants or plant cells which also express a transgenic USP receptor polypeptide, and optionally a secondary receptor polypeptide distinct from USP receptor polypeptide. Chemical substances to be tested for their ability to induce USP receptor-mediated activation of target polypeptide expression are put into contact with the transgenic plant or plant cells in varying concentrations, after which an assay for reporter gene expression is conducted to determine expression of the target polypeptide. Test substances which show activation or a statistically significant increase of target poylpeptide expression as well as test substances which show inhibition or a statistically significant decrease of target poylpeptide expression are identified as ligands of USP receptor polypeptide. The method allows test substances previously unknown to be ligands for USP in a plant cell environment to be identified as such, or a test substance suspected to be a ligand of USP in a plant cell environment to be confirmed as such. Thus it is now possible to produce ligands of the USP receptor polypeptide by performing the following process steps:

synthesizing novel test substances in accordance with routine methods known in the chemical arts;

transforming a plant cell with a USP receptor expression cassette encoding a USP receptor polypeptide and a target expression cassette encoding a target polypeptide;

culturing progeny cells of said transformed plant cells;

expressing the USP receptor polypeptide in the progeny cells;

contacting a progeny cell with a novel test substance as synthesized above; and determining expression of the target polypeptide;

repeating the previous two process steps with further novel test substances;

selecting a test substance which significantly activates or inhibits expression of the target polypeptide; and repeating chemical synthesis of the substance selected.

Ligands of USP receptor polypeptide obtainable following the process steps above constitute further subject matter of the present invention.

Additionally, this method can be used to identify antagonists, or inhibitors, of USP receptor-mediated activation of target polypeptide expression. Such antagonists are identified by their ability to reduce the ligand-induced activity of the target polypeptide expression.

Different reporter genes can be used as the target expression cassette in the screening method. One useful reporter is firefly luciferase. Its use in a target expression cassette Is described in Examples 7 and 9 below. Another useful reporter gene is GUS, or glucuronidase, which catalyzes the cleavage of a chromogenic substrate such as 5-bromo-4-chloro-3indolyl β-D-glucuronide or o-nitrophenyl-β-D-glucuronide. The GUS reporter has the advantage of producing a chromogenic reaction product which can be detected quantitatively, e.g. by spectrophotometry, or qualitatively by visual inspection. Receptor expression cassettes useful in the screening method are USP, or chimeric versions of USP such as USP-VP16 or VP16-USP.

Since USP is related in sequence to the mammalian RXRα receptor, and RXR is capable of forming heterodimers with EcR (Thomas et al., *Nature* 362: 471–475

(1993)), receptor expression cassettes which encode RXR may also be used in the screening method. In this way it may be discovered to which extent ligands for USP are useful as ligands for RXR in plant cells, or chemical substances may be identified other than juvenile hormone or one of its agonists as suitable chemical ligands for RXR in plant cells.

EXAMPLES

The following examples further describe the materials and methods used in carrying out the invention and the subsequent results. They are offered by way of illustration, and their recitation should not be considered as a limitation of the claimed invention.

Example 1

Construction of a Plant-Expressible Receptor Expression Cassette Encoding the Ecdysone Receptor The DNA coding region for the Ecdysone Receptor (EcR) of Drosophila was isolated from a cDNA library derived from Canton S pupae (day 6) prepared in λgt11 (Clontech, cat. no. IL 1005b), and from fragments generated by genomic PCR with oligonucleotides designed from the published sequence of the B1 isoform of the EcR (Koelle et al., Cell 67:59, 1991). The B1 isoform EcR sequence was confirmed by automated sequence analysis using standard methods and alignment with the published sequence (Talbot et al., Cell 73:1323, 1993). The expressed full length EcR coding region was modified to contain a BamHI site immediately upstream from the start codon using the oligonucleotide SF43 (5'-CGC GGA TCC TAA ACA ATG AAG CGG CGC TGG TCG AAC AAC GGC-3'; SEQ ID NO:1) in a PCR reaction. The plant expression vectors pMF6 and pMF7 contain a Cauliflower Mosaic Virus 35S promoter (CaMV 35S), a maize Adh1 Intron1, and a nopaline synthetase polyadenylation and termination signal (See Goff et al., Genes and Development 5:298, 1991). The vectors pMF6 and pMF7 differ only in the orientation of the polylinker used for insertion of the desired coding sequence. The full length EcR coding sequence was ligated into the plant CaMV 35S expression vector pMF6 by using the flanking BamHI restriction sites. This receptor expression cassette is referred to as 35S/EcR.

Example 2

Construction of a Plant-Expressible Receptor Expression Cassette Encoding the Ultraspiracle Receptor The cDNA encoding the native Ultraspiracle receptor (USP) of Drosophila is described by Henrich et al., Nucleic Acids Research 18:4143 (1990). The full length USP coding sequence with the flanking 5' and 3' untranslated regions was ligated into the plant expression vector pMF7 (described in Example 1) using the flanking EcoRI restriction sites. This receptor expression cassette is referred to as 35S/USP.

Example 3

Construction of a Receptor Expression Cassette having the DNA Binding Domain from GAL4 and the Ligand Binding Domain from EcR A receptor expression cassette was constructed where the DNA binding domain of EcR is replaced by the DNA binding domain of GAL4 fused at the N-terminal position. The DNA coding region for the EcR of Drosophila was obtained as described in Example 1. The coding sequence for the DNA binding domain of GAL4 was subcloned from plasmid pMA210. Ma and Ptashne, Cell, 48: 847 (1987).

A receptor expression cassette encoding a GAL4-EcR chimeric receptor polypeptide was constructed by fusion of the DNA binding domain of GAL4 to the ligand binding domain and carboxy terminus of EcR. To make the fusion, the oligonucleotide SF23 (5'-CGC GGG ATC CAT GCG GCC GGA ATG CGT CGT CCC G-3'; SEQ ID NO:2) was used to introduce by PCR a BamHI site into the cDNA sequence for EcR at the nucleotide position equivalent to amino acid residue 330 (immediately following the EcR DNA-binding domain). The resulting truncated EcR coding sequence (EcR$^{330-878}$) was subcloned into the plasmid pKS+ (Stratagene).

A subclone of GAL4 was obtained from plasmid pMA210 which contained the coding sequence of the DNA binding domain (amino acids 1–147) by subcloning the amino terminus encoding DNA sequence of GAL4 to the ClaI site into pSK+ (Stratagene) as previously described (Goff et al., Genes and Development 5:298, 1991). This plasmid was designated pSKGAL2, and was cut with ClaI and KpnI and the following double stranded oligonucleotide was inserted:

The resulting plasmid was designated pSKGAL2.3. The complete fusion 35S/GAL4-EcR$^{330-878}$ was generated using the BamHI sites in the polylinkers flanking the DNA binding domain of GAL4 in pSK+ and the EcR$^{330-878}$ moiety in pKS+. These coding sequences were ligated into the monocot expression vector pMF6 (described in Example 1) via the use of the flanking EcoRI restriction sites. This receptor expression cassette is referred to as 35S/GAL4-EcR$^{330-878}$.

Example 4

Construction of a Plant-Expressible Receptor Expression Cassette having the Ligand Binding Domain from Ultraspiracle and the Transactivation Domain from VP16

A receptor expression cassette was constructed which comprises the ligand binding domain of USP with the transactivation domain of VP16 fused to either the N-terminus or C-terminus of the USP polypeptide.

To construct the receptor expression cassette encoding a chimeric polypeptide having the transactivation domain of VP16 at the C-terminal position, the carboxy-terminus and stop codon of the cDNA for the receptor USP (described in Example 2) were removed by subcloning into pKS+ (Stratagene) using the XhoI site at USP nucleotide number 1471 of the coding sequence. The resulting USP subclone encoding amino acids 1 to 490 was fused to the transactivation domain of VP16 using the flanking KpnI restriction site of the USP subclone, and the KpnI site of pSJT1193CRF3 which encodes the carboxy-terminal 80 amino acids of VP16 (Triezenberg et al., Genes and Develop. 2: 718–729 (1988)). The resulting USP-VP16 fusion was cloned into the CaMV 35S plant expression vector pMF7 (described in Example 1) using the EcoRI and BamHI restriction enzyme sites flanking the coding sequence of USP-VP16. This receptor expression cassette is referred to as 35S/USP-VP16.

The USP derivative with the transcriptional activation domain fused to the amino-terminus was constructed by first engineering a BamHI site adjacent to the USP start codon using the oligonucleotide SF42 (5'-CGC GGA TCC ATG GAC AAC TGC GAC CAG GAC-3'; SEQ ID NO:5) in a PCR reaction. The stop codon in VP16 was eliminated and a flanking BamHI site introduced using the oligonucleotide SF37 (5'-GCG GGA TCC CCC ACC GTA CTC GTC AAT TC-3'; SEQ ID NO:6), and a start codon with a plant consensus sequence immediately upstream of the start codon as well as a BamHI site were introduced at the amino terminal end using the oligonucleotide SA115 (5'-GTC GAG CTC TCG GAT CCT AAA ACA ATG GCC CCC CCG ACC GAT GTC-3'; SEQ ID NO:7) as primers in a PCR reaction. The resulting VP16 activation domain and USP coding sequence (encoding amino acids 1 to 507) were joined in frame by the adjacent BamHI sites, and the VP16-USP coding sequence was inserted into the CaMV 35S plant expression vector pMF7 by the 5' BamHI and 3' EcoRI sites. This receptor expression cassette is referred to as 35S/VP16-USP.

Example 5

Construction of a Receptor Expression Cassette having the DNA Binding Domain and Ligand Binding Domain from EcR and the Transactivation Domain from the C1 Regulatory Gene of Maize The $EcR^{227-825}$-C1 fusion was generated by placing a start codon immediately before the EcR DNA binding domain with the oligonucleotide SF30 (5'-CGC-GGA-TCC-ATG-GGT-CGC-GAT-GAT-CTC-TCG-CCT-TC-3'; SEQ ID NO:8) used in a PCR reaction on the full length EcR coding sequence. The coding sequence for the transcriptional activation domain (amino acids 219–273) of the maize C1 protein (Goff et al. *Genes and Develop.* 5: 298–309 (1991)) was fused in frame to the coding sequence for amino acids 51 to 825 of EcR (at the EcR KpnI restriction enzyme site). The C1 transactivation domain was linked to EcR by a polylinker encoding VPGPPSRSRVSISLHA (SEQ ID NO:9). The 35S/$EcR^{227-825}$-C1 plant expression vector fusion was constructed by insertion of a BamHI fragment carrying the coding sequence into the pMF7 vector. This receptor expression cassette is referred to as 35S/$EcR^{227-825}$-C1.

Example 6

Construction of a Receptor Expression Cassette having the DNA Binding Domain from GAL4, the Ligand Binding Domain from EcR and the Transactivation Domain from the C1 Regulatory Gene of Maize A GAL4-$EcR^{330-825}$-C1 fusion was constructed using the GAL4-$EcR^{330-878}$ construct described in Example 3 and the $EcR^{227-825}$-C1 construct of Example 5. The sequence of the EcR coding region (starting at amino acid 456) was exchanged at the AatII site. This receptor expression cassette is referred to as 35S/GAL4-$EcR^{330-825}$-C1.

Example 7

Construction of a Plant-Expressible Target Expression Cassette Encoding Firefly Luciferase having the Response Element for the GAL4 DNA Binding Domain The plant-expressible target expression cassette encoding firefly luciferase having the response element for the DNA binding domain of GAL4 was constructed in the following manner. The maize Bronze-1 (Bz1) core promoter driving the synthesis of firefly luciferase was removed from the Bz1reporter pBz1LucR98 (Roth et al., *Plant Cell* 3:317, 1991) via the NheI and SphI sites and placed in a pUC6S-derived plasmid carrying the luciferase gene. The modified Bz1 core promoter contains an NheI site (GCTAGC) and Bz1promoter sequences up to nucleotide position –53 (Roth et al., *Plant Cell* 3:317,1991). Ten GAL4 binding sites were removed from the GAL4 regulated reporter pGALLuc2 (Goff et al., *Genes and Development* 5:298, 1991) by digestion with EcoRI and PstI and inserted into pBlueScript (Stratagene) using the same restriction enzyme sites. The HindIII site at the 5' end of the GAL4 binding sites was changed to a BamHI site by insertion of an HindIII/BamHI/HindIII adaptor, and the resulting BamHI fragment containing the GAL4 binding sites was removed and placed into a BglII site upstream of the Bz1core promoter driving luciferase. This target expression cassette is referred to as $(GAL4_{b.s.})_{10}$-Bz1$_{TATA}$/Luc.

Example 8

Construction of a Plant-Expressible Target Expression Cassette Encoding Firefly Luciferase having a Direct Repeat Response Element The plant-expressible target expression cassette encoding firefly luciferase having a direct repeat (DR) response element with an EcRE half site and an RXR-prefered half site was constructed in the following manner: The maize Bz1core promoter-luciferase construct in the pUC6S-derived plasmid as described in Example 7 was used as the starting point. Double-stranded synthetic oligonucleotides containing a DR RE and 3 base pair spacing between the half sites were synthesized with BamHI and BglII cohesive ends (SF77: 5'-GAT CCG TAG GGT CAC GAA AGT TCA CTC GCA-3'; SEQ ID NO:10) (SF78: 5'-GAT CTG CGA GTG AAC TTC GTG ACC CCT ACG-3'; SEQ ID NO:11), phosphorylated, annealed and ligated upstream of the Bz1core promoter by insertion into a unique BglII site. Three copies of the RE were obtained by sequential BglII digestion and insertion of additional double-stranded oligonucleotides. This target expression cassette is referred to as $(DR3)_3$-Bz1$_{TATA}$/Luc.

Example 9

Transformation of Plant Cells and Control of Target Polypeptide Expression by Receptor Polypeptides In the Presence of a Chemical Ligand Control of target polypeptide expression by various receptor polypeptides, including the chimeric receptor polypeptides of the present invention, can be shown by simultaneously transforming plant cells with the necessary gene constructions using high velocity microprojectile bombardment, followed by biochemical assay for the presence of the target polypeptide. The necessary gene constructions comprise a USP receptor expression cassette which encodes a USP receptor polypeptide (FIG. 1). Optionally, the USP receptor expression cassette may be transformed along with a secondary receptor expression cassette which encodes a receptor polypeptide distinct from USP (FIGS. 2 and 3). In addition, a target expression cassette which encodes a target polypeptide is also necessary.

The expression cassettes were simultaneously delivered to maize suspension cells cultured in liquid N6 medium (Chu et al. *Scientia Sinica* XVIII:659–668, 1975) by high velocity microprojectile bombardment using standard techniques of DNA precipation onto microprojectiles and high velocity bombardment driven by compressed helium (PDS1000/He, BioRad, Hercules, Calif.). Transfected cells were incubated in liquid suspension in the presence of the appropriate chemical ligand for approximately 48 hours in N6 media. After incubation, the transformed cells were harvested then homogenized at 0° C. Debris in the extracts was removed by centrifugation at 10,000 g at 4° C. for 5 minutes.

Target polypeptide expression was detected by assaying the extract for the presence of the product encoded by the target expression cassette. One commonly used coding sequence for the target polypeptide when testing control of expression by the receptor polypeptides in the presence of a chemical ligand is firefly luciferase. The activity of firefly luciferase is determined by quantitating the chemiluminescence produced by luciferase catalyzed phosphorylation of luciferin using ATP as substrate (Promega Luciferase Kit, cat. no. E1500), using an Analytical Luminescence Model 2001 luminometer.

Example 10

The Receptor Polypeptides GAL4-EcR$^{330-825}$C1 and USP-VP16 Activate Expression of a Target Polypeptide In Plant Cells and Activation is Blocked by Juvenile Hormone Agonists Using the transformation method of Example 9, the receptor expression cassette 35S/GAL4-EcR$^{330-825}$-C1 (Example 6), the receptor expression cassette 35S/USP-VP16 (Example 4) and the target expression cassette (GAL4$_{b.s.}$)$_{10}$-Bz1$_{TATA}$/Luc (Example 7) were co-transformed into maize cells. Transformed cells were incubated in the presence of 10 μM Fenoxycarb or Methoprene as chemical ligands for approximately 48 hours. Luciferase assays were performed as described in Example 9. The results are presented in Table 1.

TABLE 1

| Receptor | Chemical Ligand | Luciferase Activity (light units) |
| --- | --- | --- |
| Experiment #1 | | |
| None | None | 2,503 |
| 35S/GAL4-EcR$^{330-825}$-C1 + 35S/USP-VP16 | None | 277,862 |
| 35S/GAL4-EcR$^{330-825}$-C1 + 35S/USP-VP16 | Fenoxycarb | 77,418 |
| 35S/GAL4-EcR$^{330-825}$-C1 + 35S/USP-VP16 | Methoprene | 14,786 |
| Experiment #2 | | |
| None | None | 1,302 |
| 35S/GAL4-EcR$^{330-825}$-C1 + 35S/USP-VP16 | None | 178,092 |
| 35S/GAL4-EcR$^{330-825}$-C1 + 35S/VSP-VP16 | Methoprene | 5,730 |

The above results show that the 5' regulatory region of the target expression cassette comprising the GAL4 response elements can be activated in plant cells by the receptor polypeptides GAL4-EcR-C1 and USP-VP16, and that this activation is reversed in the presence of a juvenile hormone agonist. The level of expression of the target polypeptide luciferase was 3.5- to 31-fold lower in the presence of the juvenile hormone agonists compared to their absence.

Example 11

The Receptor Polypeptides GAL4-EcR$^{330-825}$-C1 and USP-VP16 Activate Expression of a Target Polypeptide in Plant Cells and Activation is Blocked by Juvenile Hormone Agonists Using the transformation method of Example 9, the receptor expression cassette 35S/GAL4-EcR$^{330-825}$-C1 (Example 6), the receptor expression cassette 35S/USP-VP16 (Example 4) and the target expression cassette (GAL4$_{b.s.}$)$_{10}$-Bz1$_{TATA}$/Luc (Example 7) were co-transformed into maize cells. Transformed cells were incubated in the presence of 10 μM tebufenozide with and without 10 μM Fenoxycarb or Methoprene as chemical ligands for approximately 48 hours. Luciferase assays were perfomed as described in Example 9. The results are presented in Table 2.

TABLE 2

| Receptor | Chemical Ligand | Luciferase Activity (light units) |
| --- | --- | --- |
| None | None | 1,302 |
| 35S/GAL4-EcR$^{330-825}$-C1 + 35S/USP-VP16 | None | 178,092 |
| 35S/GAL4-EcR$^{330-825}$-C1 + 35S/USP-VP16 | Tebufenozide | 908,912 |
| 35S/GAL4-EcR$^{330-825}$-C1 + 35S/USP-VP16 | Tebufenozide + Methoprene | 159,873 |

The above results show that the 5' regulatory region of the target expression cassette comprising the GAL4 response elements can be activated in plant cells by the receptor polypeptides GAL4-EcR-C1 and USP-VP16 in response to the chemical ligand tebufenozide, and that this activation is blocked in the presence of the juvenile hormone agonist methoprene. The level of tebufenozide-induced activation of luciferase gene expression was approximately 6-fold increased when used alone, and completely blocked by the presence of the juvenile hormone agonist methoprene.

Example 12

The Receptor Polypeptide VP16-USP Activates Expression of a Target Polypeptide in Plant Cells Using the transformation method of Example 9, plasmids containing the receptor expression cassette 35S/VP16-USP (Example 4) and the target expression cassette (DR3)$_3$-Bz1$_{TATA}$/Luc (Example 8) were co-transformed into maize cells. Transformed cells were incubated in the presence of 10 μM Methoprene as chemical ligand for 48 hours. Luciferase assays were performed as described in Example 9. The results are presented in Table 3.

TABLE 3

| Receptor | Chemical Ligand | Luciferase Activity (light units) |
| --- | --- | --- |
| None | None | 5,690 |
| 35S/VP16-USP | None | 29,967 |
| 35S/VP16-USP | Methoprene | 485,458 |

The above results show that the 5' regulatory region of the target expression cassette comprising the Direct Repeat response elements can be activated in plant cells by the receptor polypeptide VP16 -USP In the presence of a juvenile hormone agonist. The level of expression of the target polypeptide luciferase was about 16-fold above that observed in the absence of the juvenile hormone agonist.

Example 13

Construction of Vectors for Transforming Arabidopsis Plants which Express EcR, USP, or RXR Derivatives and Carry a Receptor-regulated Reporter Agrobacterium T-DNA vector plasmids were constructed from the previously described plasmids pGPTV-Kan and pGPTV-Hyg (Becker et al., *Plant Mol. Biol.* 20:1195–1197, (1992)). The SacI/HindIII uidA (GUS) reporter gene of both the pGPTV-Kan and pGPTV-Hyg plasmids was replaced by the SacI/HindIII polylinker from pGEM4Zf(+), pSPORT1, pBluescriptKS(+), pIC20H, or pUC18 to give the plasmids pSGCFW, pSGCFX, pSGCFY, pSGCFZ, pSGCGA, pSGCGC, pSGCGD, pSGCGE, pSGCGF, and pSGCGG respectively. A GAL4-regulated luciferase reporter as the target expression cassette was constructed as a T-DNA Agrobacterium plasmid by first subcloning a 328 bp KpnI/HindIII fragment with 10 GAL4 binding sites and a maize Bronze-1 TATA as described in Example 7 into the KpnI/HindIII sites of the modified luciferase reporter plasmid pSPLuc+ (Promega) to create plasmid pSGCFO1. A 1.991 Kb KpnI/XbaI fragment from pSGCFO1 containing the GAL4 binding sites-Bz1TATA-Luciferase reporter was subcloned into a T-DNA vector via ligation to a 7.194 NdeI/SpeI fragment of pSGCFX1 and a 4.111 NdeI/KpnI fragment of pSGCFZ1 described above. The resulting plasmid was designated pSGCGL1, and carries a NPTII selectable marker driven by a nos promoter conferring resistance to kanamycin in the transgenic plant, and a GAL4-regulated luciferase reporter. A GAL4-regulated GUS reporter with 10 GAL4 binding sites, a 35S TATA region and GUS coding region was constructed in a similar manner and was designated pAT86. A direct repeat (DR) response element reporter with 3 copies of the DR RE, a Bz1 TATA, a luciferase coding region, and a nos terminator analogous to that described in Example 8 was also constructed in a manner similar to that described for pSGCGL1, and was designated pSGCHU1. Receptor expression cassettes described in examples 3–6 above were used to construct analogous Agrobacterium T-DNA constructs carrying the CaMV 35S promoter and the nos polyadenylation signals. Single and double receptor constructs were generated by subcloning the appropriate expression cassette into the GAL4-Luciferase reporter pSGCGL1.

Example 14

Generation of Transgenic Arabidopsis Expressing VP16-USP and Carrying a DR-Luciferase Reporter

*Arabidopsis thaliana* (Columbia) was transformed with an Agrobacterium vector harboring a CaMV 35S promoter and a DR-Luciferase reporter (as described in Example 13 above) by the following vacuum-infiltration procedure. Electrocompetent GV3101 Agrobacterium cells were prepared by incubating GV3101 Agrobacterium in 2xYT media at 28° C. with aeration for 24–30 hours to an $OD_{600}$ of 0.5–0.7 units. Cells were chilled on ice for 10–30 minutes, and centrifuged at 5,000 RPM for 5 minutes at 4° C. The supernatant was discarded, and the cell pellet resuspended in 1 volume of ice-cold 10% glycerol. Cells were again centrifuged at 5,000 RPM for 5 minutes at 4° C. The supernatant was discarded, and the cell pellet resuspended in 0.05 volumes of ice-cold 10% glycerol. Cells were again centrifuged at 5,000 RPM for 5 minutes at 4° C. The supernatant was discarded, and the cell pellet resuspended in 0.02 volume of ice-cold 10% glycerol. Cells were again centrifuged at 5,000 RPM for 5 minutes at 4° C. The supernatant was discarded, and the cell pellet resuspended 0.02 volume of ice-cold 10% glycerol. Cells were again centrifuged at 5,000 RPM for 5 minutes at 4° C. The supernatant was discarded, and the cell pellet resuspended in 0.01 volume of ice-cold 10% glycerol. Cells were aliquoted in 200 ml amounts per 1.5 ml microfuge tubes, quick-frozen in liquid $N_2$, and stored at −80° C. Electrocompetent cells were used before 6 weeks storage at −80° C. Frozen electrocompetent cells were thawed on ice and 40 ml transfered to a prechilled 1.5 ml microfuge tube. 1 ml of the appropriate Agrobacterium plasmid DNA (2–10 ng) was added to the thawed cells and mixed on ice. The cell/plasmid mixture was transfered to a prechilled 0.2 cm Bio-Rad electroporation cuvette, and electroporated at 2.0 KVolts, 600 Ohms, 25 μFarad, with a 6 msec time constant. 1 †ml of 2xYT media was added to the electroporation cuvette, the cell/plasmid solution was mixed with a pipet tip, and the contents transfered to a fresh 1.5 ml microfuge tube. Cells were then incubated at 37° C. for 1 hour on a shaker at 200 RPM. The cells were centrifuged down for 2 minutes at a setting of 6 in an Eppendorph adjustable-speed microfuge, the supernatant decanted, and the cell pellet resuspended in the remaining liquid. Resuspended cells were spread on an LB media plate with the appropriate antibiotic. Plates were incubated at 28–30° C. for 2–43 days. A 50 ml LB culture was innoculated with a single transformed colony in a 250 ml flask with Rifampicin at 100 μg/ml and Gentomycin at 25 μg/ml and Kanamycin at 100 μg/ml. The culture was incubated for 24–36 hours at 28° C. at 250 RPM and 10 ml of the culture was used to innoculate 500 ml LB+antibiotics in a 2-liter flask. This culture was incubated overnight at 28° C. with shaking at 250 RPM. Plasmid DNA was isolated from this Agrobacterium culture and verified by restriction analysis.

Arabidopsis plants were grown in mesh covered soil in 3 inch square plastic pots in a phytotron set for 16 hours light, 8 hours dark, 20° C. for 4–5 weeks. Plants were grown until the floral meristem was approximately 2 inches tall. Floral meristems of Arabidopsis plants to be transformed were removed two days prior to exposure to Agrobacterium. The Agrobacterium culture was centrifuged at 5000 RPM for 5 minutes and the resulting pellet resuspended in 500 ml of Infiltration Media (4.3 g MS salts/liter, 5% Sucrose, 0.01 mg/ml benzylaminopurine, 100 ml/liter Silwet L77, pH 5.8). Arabidopsis plants were soaked in water to saturate the soil. 500 ml of the bacterial cell suspension was transferred to the bottom of a sterile vacuum dessicator, and the Arabidopsis plants in their pots were placed top down in the Agrobacterium solution. Vacuum was applied to the dessicator for 5 minutes, then released slowly. This vacuum treatment was repeated three times, plants were rinsed of excess Agrobacterium, and returned to the growth chamber. The vacuum-infiltrated plants were allowed to mature, flower, and produce seed. The resulting seed was further dried out in a drying room with low humidity at 95° C. for approximately 5–10 days. The seed was removed from the dried flowers by crushing, then filtered through a 425 micron mesh sieve. It takes ca. 5 weeks to get seed after vacuum infiltration. Once completely dry, approximately 240 mg of seed was sterilized by addition to 1 ml 70% EtOH, vortexed thoroughly, and incubated for 2 minutes at room temperature. Seed was centrifuged briefly at high speed in an Eppendorf Microfuge, and the supernatant was removed. Pelleted seed was resuspended in 1 ml sterlization buffer (1 part 10% Triton X-100, 10 parts bleach, 20 parts dd $H_2O$), vortexed, and incubated at room temperature for 30 minutes. Seed was centrifuged briefly at high speed in an Eppendorph Microfuge, and the supernatant was removed. Seed was resuspended in 1 ml sterile dd $H_2O$, vortexed, centrifuged at high speed in a microfuge, and the supernatant removed. This wash step was repeated three times, then the seed was transferred to a 50 ml centrifuge tube for a final wash in 5 ml dd $H_2O$. Seed was briefly centrifuged at top speed in a Beckman table top centrifuge. The supernatant was decanted, and seed was resuspended in 24 ml of sterile 0.8 w/v% low melting point agarose at 50° C., mixed, and 8 ml was aliquoted to each of three 150 mm germination medium (GM) plates (Murashige and Skoog, Physiol Plant 15: 473497, 1962). containing antibiotic for selection (either 50 μg/ml Kanamycin or 50 μg/ml Hygromycin) and 500 μg/ml carbenicillin. The plated seed was incubated at 4° C. in the dark for 24 hr, then moved into a growth chamber set at 20° C. 16 hours light, 8 hours dark cycle per day. Germinated seedlings were selected on plates for 5–10 days, plantlets were transplanted to fresh selection plates, and transplanted to soil following 5–10 days further selection. Freshly transplanted plantlets were covered with plastic wrap for 2–3 days, then grown until initiation of the floral meristems.

Example 15

Chemical Induction of Isolated Transgenic Plant Tissues

Transgenic plants were tested for inducible gene expression by the following technique. Two leaves of approximately the same size were removed from the transgenic plant, and incubated in water containing 50 μg/ml Kanamycin (or 25 μg/ml hygromycin if the transgene carried this marker), with either 0.1% ethanol or 0.1% ethanol and 10 μM methoprene or fenoxycarb. The leaves were Incubated for approximately 24 hours under the standard growth conditions described in Example 14. Following incubation with inducing compound, a leaf extract was prepared by homogenization of the leaf in 500 μl 100 mM $KPO_4$ 1 mM DTT, pH 7.8 buffer at 0° C. Extracts were centrifuged for 5 minutes in an Eppendorf Microfuge at 4° C., and stored at 0° C. until assayed. Luciferase activity in each extract was determined using an Analytical Luminescence Model 2010 Luminometer, and the Promega Luciferase Assay System according to the recommendations of the manufacturer. Extract protein concentration was determined using the Pierce BCA Protein Assay (Smith et al., *Anal. Biochem.* 150: 76–85). Luciferase values are expressed as light units per 10 seconds at room temperature per 100 μg extract protein. Fenoxycarb treatment resulted in a 6.2-fold increase in luciferase activity and methoprene resulted in a 25-fold increase In luciferase activity as shown in Table 4 below.

TABLE 4

| Receptor | Chemical Ligand | Luciferase Activity (light units) |
| --- | --- | --- |
| None | None | 638 |
| 35S/VP16-USP | Fenoxycarb | 3,991 |
| 35S/VP16-USP | Methoprene | 15,790 |

Example 16

Screening for New Ligands Which bind to USP Using Transgenic Plant or Plant Cells Expressing USP or RXR Derivatives and Carrying a Receptor-regulated Reporter New ligands for USP or RXR which are effective in a plant cell environment can be discovered by using a screening method based on the expression of a receptor-regulated reporter as target expression cassette in transgenic plants or plant cells which also express the appropriate receptor polypeptide. In this way, chemical substances to be tested for their ability to mediate USP or RXR activation of target polypeptide expression put into contact with a transgenic plant or plant cells in varying concentrations, after which an assay for reporter gene expression is conducted. For example, 1) transgenic plants or plant cells carrying a GAL4-regulated luciferase reporter as target expression cassette and receptor expression cassettes for GAL4-EcR and USP-VP16 can be exposed to the substances to be tested and compared to unexposed plants using a light amplification instrument such as the Hamamatsu Light Detection Device, 2) transgenic plants or plant cells carrying a GAL4-regulated GUS reporter as target expression cassette and receptor expression cassettes for GAL4-EcR-C1 and VP16-RXR can be exposed to the substances to be tested and compared to unexposed plants for their ability to catalyze cleavage of a chromogenic substrate such as 5-bromo-4-chloro-3-indolyl β-D-glucuronide or o-nitrophenyl-β-D-glucuronide, 3) transgenic plants or plant cells carrying a DR RE-regulated luciferase reporter and an expression cassette for VP16-USP can be exposed to the substances to be tested and compared to unexposed plants using a light amplification instrument such as the Hamamatsu Light Detection Device. Positive controls that may find usefulness in the above screening methods include but are not limited to tebufenozide and methoprene. In each of the above instances, a greater level of detection of the expression of the target polypeptide in the presence of a test substance compared to the level of expression in the absence of the test substance indicates that the substance tested is a ligand for either USP or RXR depending on the receptor expression cassette used in the method. In this way, test substances previously unknown to be ligands for USP in a plant cell environment may be identified as such, or a test substance suspected to be a ligand for USP in a plant cell environment can be confirmed as such.

Example 17

Isolation of Receptor Polypeptide Mutants Having Lowered Basal Activity

Mutations in the ligand binding domain of the Ultraspiracle receptor (USP) were generated in vitro using PCR mutagenesis as described by Leung et al., *Technique* 1: 11–15 (1989). PCR fragments of mutated USP ligand binding domain were cloned into a yeast expression vector operably linked to the transcriptional activation domain of VP16. Mutant constructs were transformed into the yeast GAL4 reporter strain GGY1::171. Yeast transformants were plated on media containing the indicator X-Gal. Mutants having a decreased basal level of USP receptor polypeptide activity for the heterodimer generated white to light blue colonies on X-Gal indicator plates, while the transformants expressing non-mutagenized USP receptor polypeptide generated dark blue colonies. White to light blue colonies were tested for the basal and chemical ligand-induced level of receptor polypeptide activity by growing yeast cells representing those selected colonies in S media containing glycerol, ethanol and galactose as carbon sources. The resulting culture was split into two portions, one of which was treated with juvenile hormone or one of its agonists and the other was used as a control in the absence of chemical ligand. After exposure to juvenile hormone or one of its agonists, both the treated and control portions of the culture were assayed for β-galactosidase activity according to the procedure of Miller (*Experiments in Molecular Genetics,* p. 352–355, J. H. Miller, Ed., Cold Spring Harbor Laboratory, Cold Spring Harbor, N.Y., 1972). The nucleotide sequences which encode the mutant receptor polypeptides isolated and identified by this technique are candidates for further testing since the receptor polypeptides that they encode may exhibit, in plant cells, a decreased basal activity, a greater fold induction of target gene expression in the presence of juvenile hormone or one of its agonists, or a different response to different agonists of juvenile hormone.

Example 18

Identification of Mutant Receptor Polypeptides with Improved Function in Plant Cells Receptor expression cassettes which encode the mutated USP receptor polypeptides of Example 15 were prepared according to the above Examples 2 and 4. These receptor expression cassettes, In combination with the target expression cassettes of Example 8 were transformed into plant cells according to the procedure of Example 9. Transformed plant cells were tested for activation of the 5'-regulatory region of the target expression cassette by the mutant receptor polypeptides in the presence of juvenile hormone or one of its agonists. Mutant USP receptor polypeptides which produce, in plant cells, low basal expression of a target polypeptide in the absence of chemical ligand and high expression of target polypeptide in the presence of juvenile hormone or one of its agonists are useful for controlling gene expression in plants.

Example 19

Raising Progeny of the Transgenic Plants

Transformed plants of Arabidopsis thaliana (Columbia) prepared in Example 14 are grown in mesh covered soil in 3 inch square plastic pots in a phytotron set for 16 hours light, 8 hours dark, 20° C. for 4–5 weeks. The plants contain integrated into their genome foreign DNA in the form of the receptor and target expression cassettes according to the invention. Said integrated DNA is transferred from one plant generation to the next through the process of fertilization, as a consequence of the life cycle of the transformed plant.

Fertilization is a process by which the male gametophyte and the sporophytic or gametophytic female tissues interact to achieve the successful production of a zygote. Mature pollen grains are produced in the anthers of the flower and are deposited on the surface of the stigma (pollination), where it hydrates and germinates to grow a pollen tube. The sperm cells in the pollen tube are delivered to the embryo sac present in the ovary (gynoecium) where the actual events of fertilization (gamete fusion) take place to produce the zygote. The zygote, in the form of a seed, is the realization of the next generation of a plant line. This next generation is termed the 'progeny' of the transformed plant.

The progeny may be formed by self-fertilization, wherein the male gametophyte and female gametophytic tissue arise from the same individual plant. This means that a single plant is the source of the genomic DNA for the next generation. Alternatively, progeny may be produced by cross-fertilization of two separate plants by placing the male gametophyte from one plant into contact with the female sporophytic tissues of a separate plant in order to produce the next generation of plants. In this case the genomic DNA of the progeny is derived from two separate plants. Furthermore, when a transformed plant is cross-fertilized with a non-transformed plant, the genomic DNA of the progeny is composed of transgenic genomic DNA from one plant and non-transgenic genomic DNA from a separate plant. Regardless of whether the progeny of the transformed plant are produced by self-fertilization or cross-fertilization, some of the progeny will receive an unequal genetic contribution due to the presence of the foreign DNA integrated into the genome. This unequal genetic contribution can be ascertained using the techniques of classical genetics and molecular biology.

To produce the next generation of plants containing the receptor and target expression cassettes according to the invention, the original transformed plants are allowed to mature, flower, and produce seed under controlled environmental conditions. The resulting seed is further dried out in a drying room with low humidity at 95° F. for approximately 5–10 days. The seed is removed from the dried flowers by crushing the siliques and then filtering through a 425 µm mesh sieve to separate the seed from other plant material. The seed can then be used to raise further generations of plants.

This process of producing a next generation of transformed plants, although described for Arabidopsis, is generally applicable to all angiosperm plants having integrated into their genome the receptor and target expression cassettes according to the invention.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method of controlling gene expression in a transgenic plant cell transformed with an Ultraspiracle (USP) receptor expression cassette that encodes a USP receptor polypeptide and a target expression cassette that encodes a target polypeptide, comprising:
    a) expressing the receptor polypeptide in said transgenic plant cell; and
    b) contacting said transgenic plant cell with juvenile hormone or one of its agonists, wherein the receptor polypeptide controls expression of the target polypeptide in the presence of juvenile hormone or one of its agonists.

2. The method according to claim 1 wherein expression of the target polypeptide is increased or activated in the presence of juvenile hormone or one of its agonists.

3. The method according to claim 1 wherein expression of the target polypeptide is decreased or inhibited in the presence of juvenile hormone or one of its agonists.

4. The method according to claim 1 wherein the USP receptor polypeptide comprises a heterologous transactivation domain.

5. The method according to claim 1 wherein said agonist is selected from the group consisting of fenoxycarb, diofenolan, kinoprene, methoprene, hyrdoprene, diofenolan, methoprene acid, triflumuron, hexamflumuron, teflubenzuron, flufenoxuron, flucycloxuron, lufenuron, diflubenzuron and chlorfluzuron.

6. The method according to claim 1 wherein said target expression cassette comprises a 5' regulatory region comprising between 1 and 11 copies of a response element.

7. The method according to claim 1 wherein said transgenic plant cell additionally comprises a secondary receptor expression cassette encoding a secondary receptor polypeptide distinct from the USP receptor polypeptide.

8. The method according to claim 1 wherein said transgenic plant cell is a maize cell.

9. The method according to claim 1 wherein said transgenic plant cell is a wheat cell.

10. The method according to claim 1 wherein said USP receptor expression cassette comprises an anther-specific promoter operably linked to the coding sequence for the USP receptor polypeptide.

11. The method according to claim 1 wherein said USP receptor expression cassette comprises a pistil-specific promoter operably linked to the coding sequence for the USP receptor polypeptide.

12. The method according to claim 1 wherein said target polypeptide is the ribonuclease barnase.

13. The method according to claim 1 wherein said target polypeptide is the ribonuclease inhibitor barstar.

14. The method according to claim 4 wherein said heterologous transactivation domain is the transactivation domain from the VP16 protein of herpes simplex.

15. The method according to claim 7 wherein said secondary receptor polypeptide is selected from the group consisting of Ecdysone Receptor (EcR), Drosophila Hormone Receptor 38 (DHR38), and Retinoic X Receptor (RXR).

16. A method of controlling gene expression in a transgenic plant cell transformed with a USP receptor expression cassette that encodes a USP receptor polypeptide and a target expression cassette that encodes an anti-sense sequence comprising:
    a) expressing the receptor polypeptide in said transgenic plant cell; and
    b) contacting said transgenic plant cell with juvenile hormone or one of its agonists, wherein the receptor polypeptide controls expression of the antisense sequence in the presence of juvenile hormone or one of its agonists.

17. A method of controlling gene expression, comprising the steps of:
   a) providing a transgenic plant or plant cell transformed with chimeric DNA comprising:
      i) a USP receptor expression cassette that encodes a USP receptor polypeptide, and
      ii) a target expression cassette that encodes a target polypeptide;
   b) expressing said receptor polypeptide in said transgenic plant or plant cell; and
   c) contacting said transgenic plant or plant cell with juvenile hormone or one of its agonists, wherein the receptor polypeptide controls expression of the target polypeptide in the presence of juvenile hormone or one of its agonists.

18. The method according to claim 17 wherein said transgenic plant or plant cell additionally comprises a secondary receptor expression cassette encoding a secondary receptor polypeptide distinct from the USP receptor polypeptide.

19. The method according to claim 17 wherein expression of said target polypeptide is increased or activated in the presence of juvenile hormone or one of its agonists.

20. The method according to claim 17 wherein expression of said target polypeptide is decreased or inhibited in the presence of juvenile hormone or one of its agonists.

21. The method according to claim 17 wherein said USP receptor polypeptide comprises a heterologous transactivation domain.

22. The method according to claim 17 wherein the agonist is selected from the group consisting of fenoxycarb, diofenolan, kinoprene, methoprene, hyrdoprene, diofenolan, methoprene acid, triflumuron, hexamflumuron, teflubenzuron, flufenoxuron, flucycloxuron, lufenuron, diflubenzuron, and chlorfluzuron.

23. The method according to claim 17 wherein said target expression cassette comprises a 5' regulatory region comprising between 1 and 11 copies of a response element.

24. The method according to claim 17 wherein said transgenic plant or plant cell is maize.

25. The method according to claim 17 wherein said transgenic plant or plant cell is wheat.

26. The method according to claim 17 wherein said USP receptor expression cassette comprises an anther-specific promoter operably linked to the coding sequence for the USP receptor polypeptide.

27. The method according to claim 17 wherein said USP receptor expression cassette comprises a pistil-specific promoter operably linked to the coding sequence for the USP receptor polypeptide.

28. The method according to claim 17 wherein said target polypeptide is the ribonuclease barnase.

29. The method according to claim 17 wherein said target polypeptide is the ribonuclease inhibitor barstar.

30. The method according to claim 18 wherein said secondary receptor polypeptide is selected from the group consisting of EcR, DHR38, and RXR.

31. The method according to claim 21 wherein said heterologous transactivation domain is the transactivation domain from the VP16 protein of herpes simplex.

32. A method of controlling gene expression, comprising the steps of:
   a) providing a transgenic plant or plant cell transformed with chimeric DNA comprising:
      i) a USP receptor expression cassette that encodes a USP receptor polypeptide, and
      ii) a target expression cassette that encodes an antisense sequence;
   b) expressing said receptor polypeptide in said transgenic plant or plant cell; and
   c) contacting said transgenic plant or plant cell with juvenile hormone or one of its agonists, wherein the receptor polypeptide controls expression of the antisense sequence in the presence of juvenile hormone or one of its agonists.

* * * * *